United States Patent
Bentz et al.

(10) Patent No.: US 12,285,355 B2
(45) Date of Patent: *Apr. 29, 2025

(54) THERMAL SYSTEM WITH THERMAL PAD FILTERS

(71) Applicant: Stryker Corporation, Kalamazoo, MI (US)

(72) Inventors: Andrew M. Bentz, Mattawan, MI (US); Christopher John Hopper, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 30 days.

This patent is subject to a terminal disclaimer.

(21) Appl. No.: 18/080,344

(22) Filed: Dec. 13, 2022

(65) Prior Publication Data

US 2024/0189142 A1   Jun. 13, 2024

Related U.S. Application Data

(63) Continuation of application No. 16/710,065, filed on Dec. 11, 2019, now Pat. No. 11,554,040.

(60) Provisional application No. 62/778,034, filed on Dec. 11, 2018.

(51) Int. Cl.
| | |
|---|---|
| *A61F 7/08* | (2006.01) |
| *A61F 7/00* | (2006.01) |
| *B01D 29/00* | (2006.01) |

(52) U.S. Cl.
CPC ............. *A61F 7/08* (2013.01); *A61F 7/0085* (2013.01); *B01D 29/00* (2013.01); *A61F 2007/0054* (2013.01); *A61F 2007/0056* (2013.01); *A61F 2007/0086* (2013.01)

(58) Field of Classification Search
CPC ...... A61F 2007/0063; A61F 2007/0069; A61F 2007/0086; A61F 2007/0257; A61F 2007/0258; A61F 2007/0273; A61F 2007/0274; A61F 7/0085; A61F 7/08; B01D 29/0018

See application file for complete search history.

(56) References Cited

U.S. PATENT DOCUMENTS

| | | | |
|---|---|---|---|
| 2004/0149711 A1* | 8/2004 | Wyatt | A61F 7/007 219/217 |
| 2017/0095649 A1* | 4/2017 | Vase | A61M 27/006 |
| 2017/0246030 A1* | 8/2017 | Lewis | A61L 2/22 |

* cited by examiner

*Primary Examiner* — Tigist S Demie

(74) *Attorney, Agent, or Firm* — Warner Norcross + Judd LLP

(57) ABSTRACT

A thermal pad is adapted to be placed in physical contact with a patient and to receive temperature controlled fluid from a thermal control unit. The temperature controlled fluid circulates through the thermal pad and controls the patient's temperature. The thermal pad includes first and second sheets that are sealed together about their periphery to define a fluid chamber there between. A fluid inlet and fluid outlet are fluidly coupled to the fluid chamber. In some embodiments, a filter sheet is sandwiched between the first and second sheets and arranged such that fluid entering the fluid inlet must pass through the filter sheet before exiting out of the fluid outlet. A plurality of bonds may be included that seal the first and second sheets together at a plurality of locations. In some embodiments, a non-sheet filter is positioned within the fluid chamber and filters the circulating fluid.

20 Claims, 12 Drawing Sheets

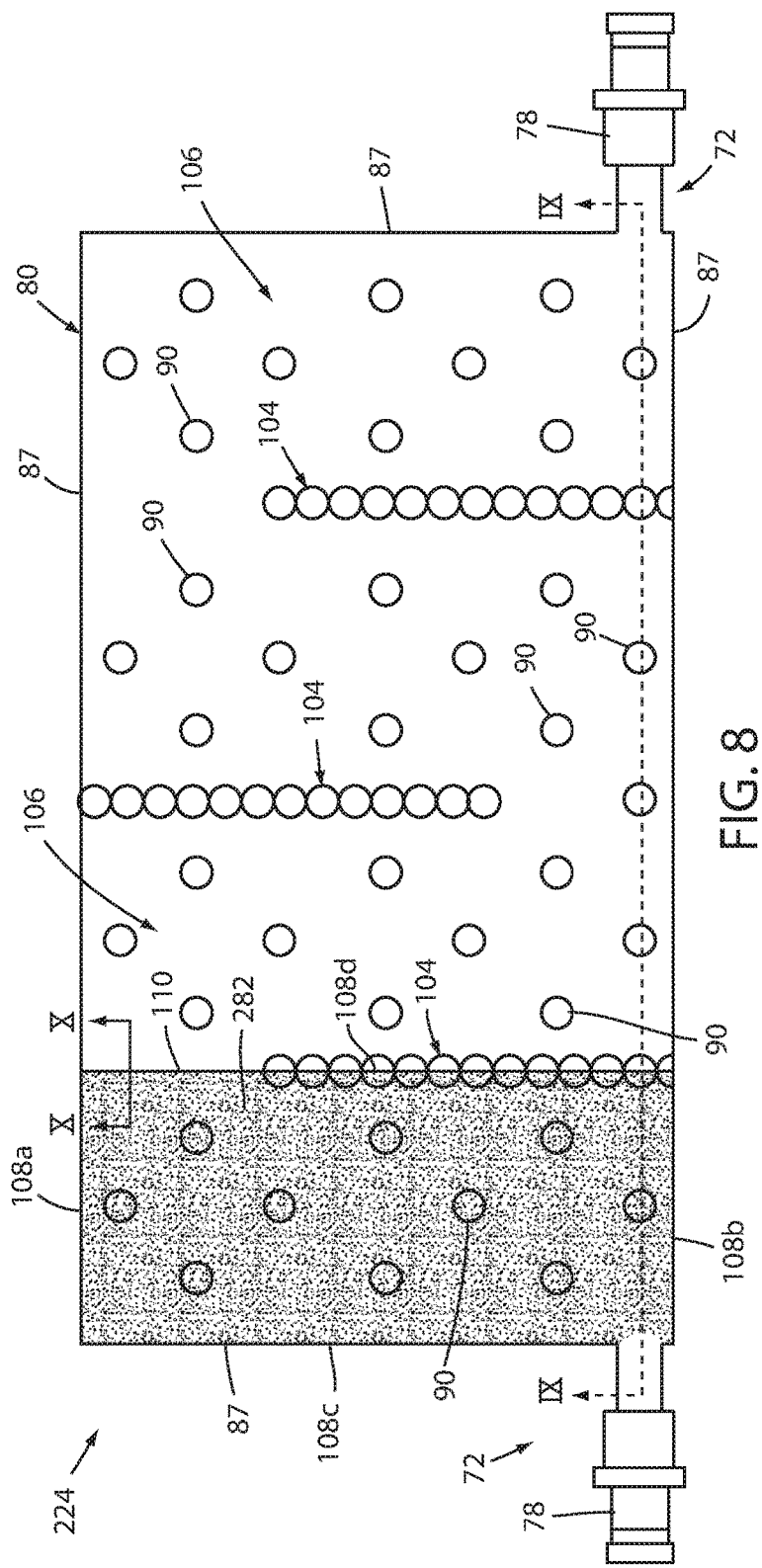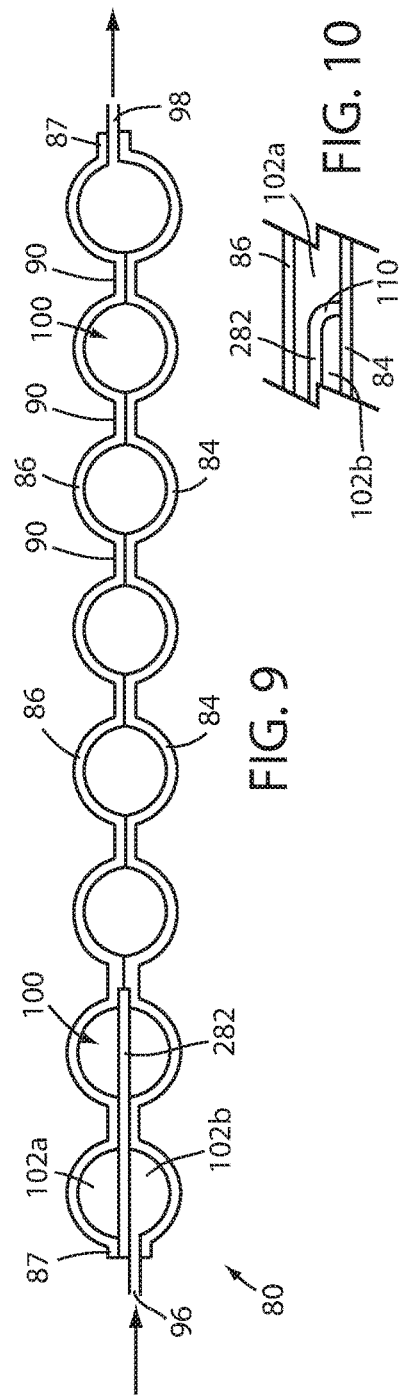

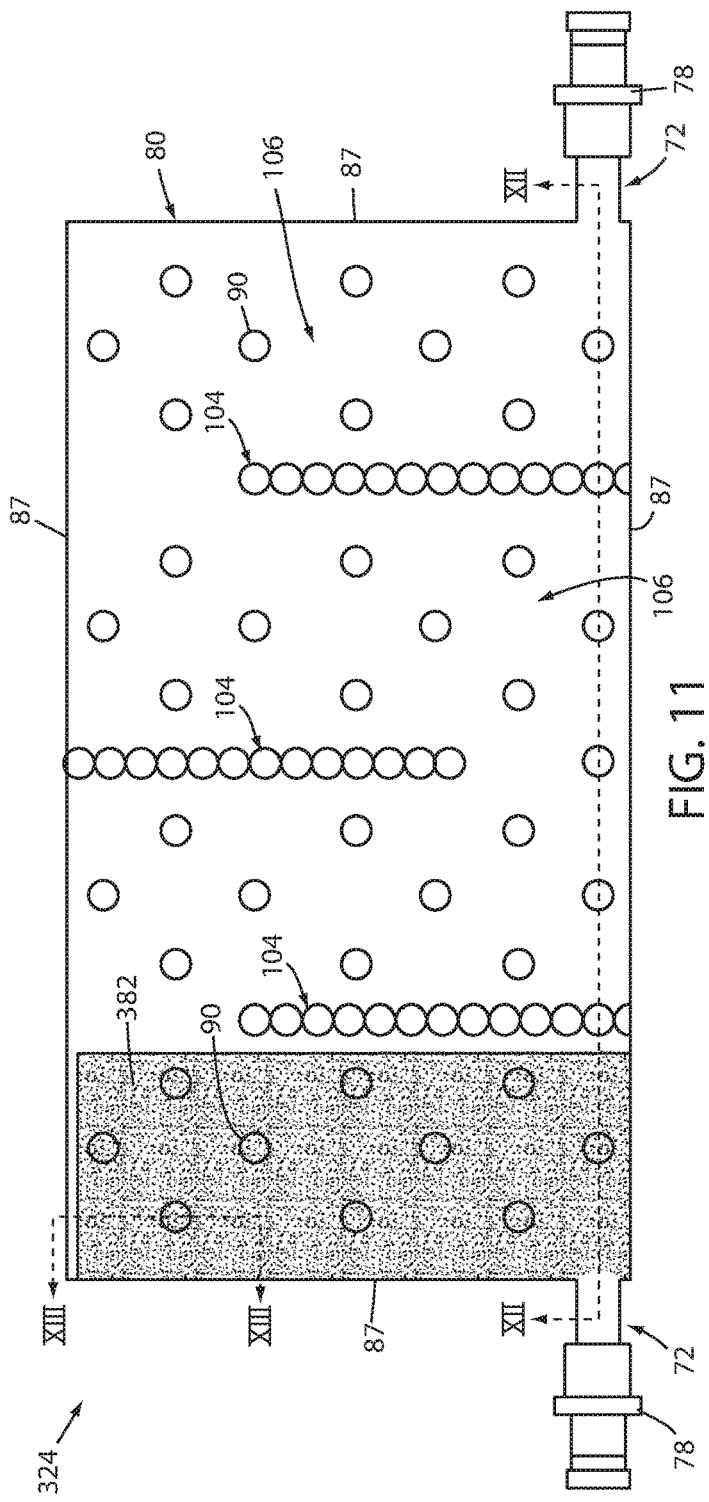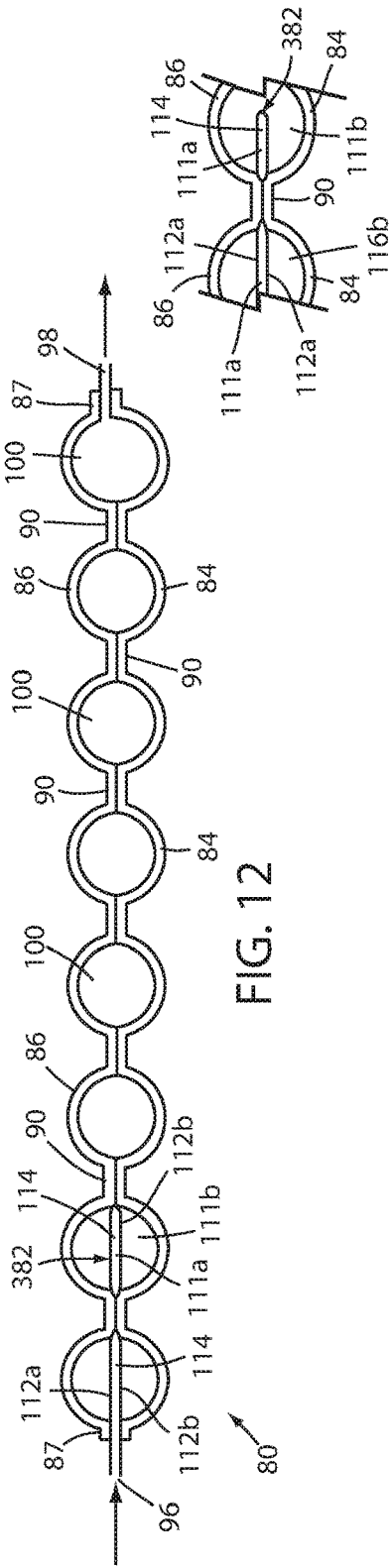

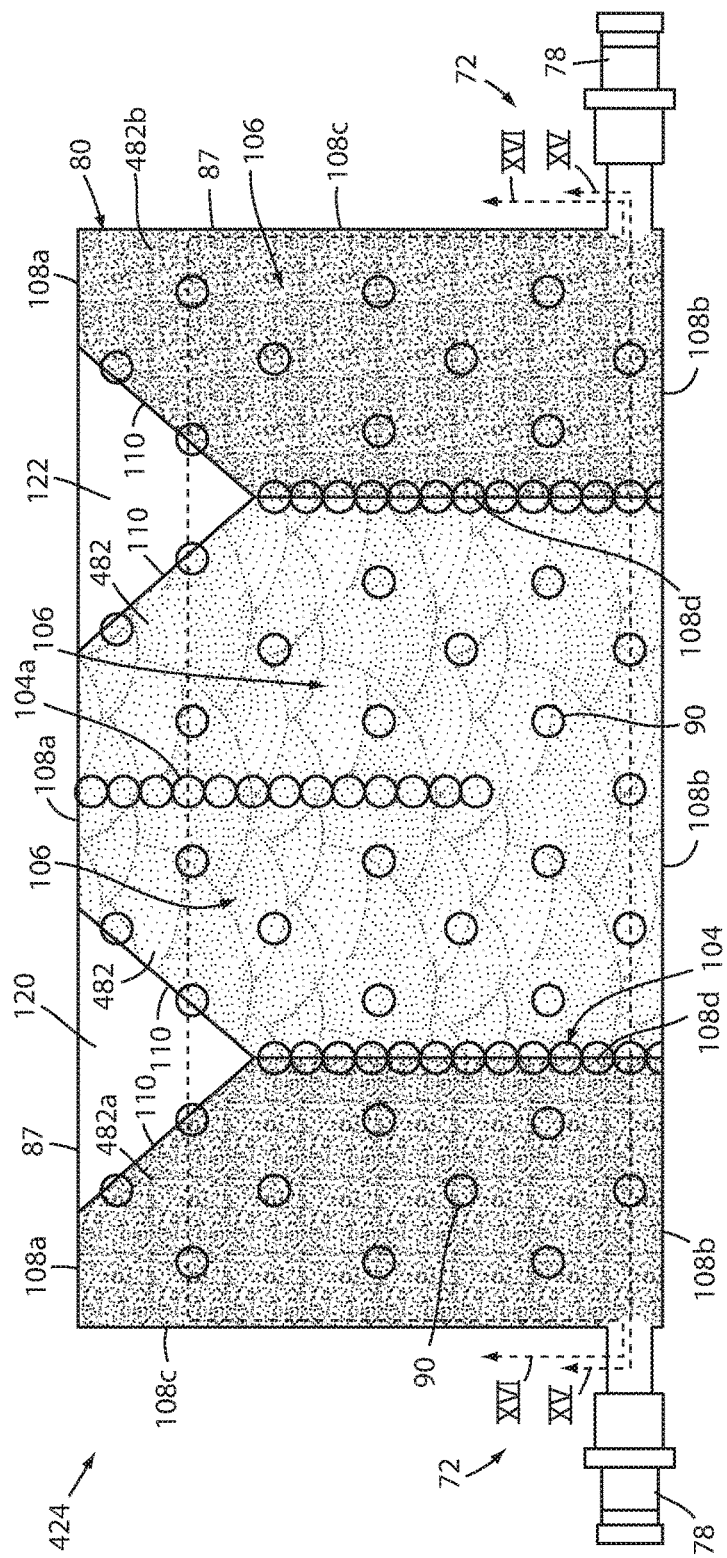
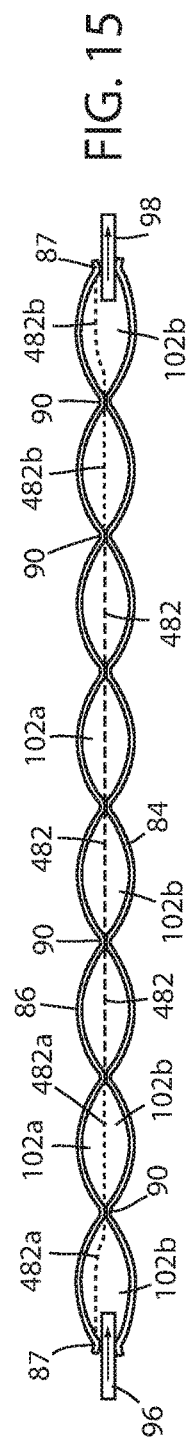
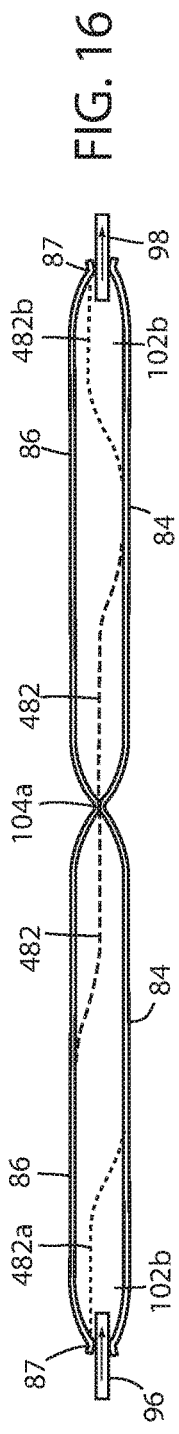
FIG. 14
FIG. 15
FIG. 16

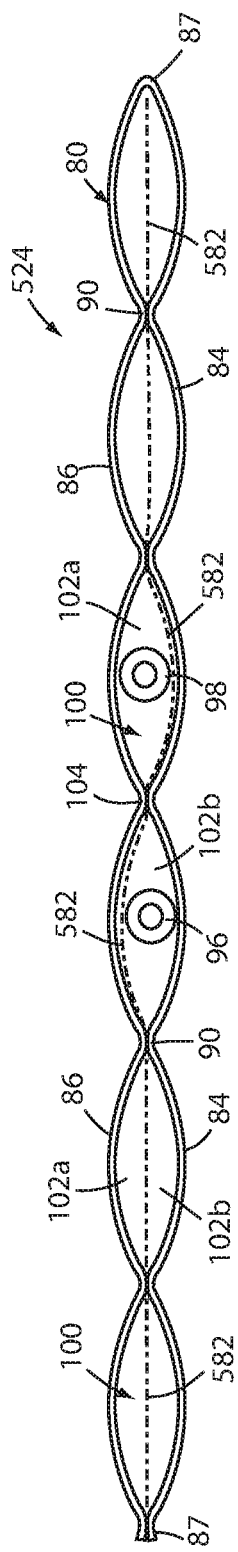
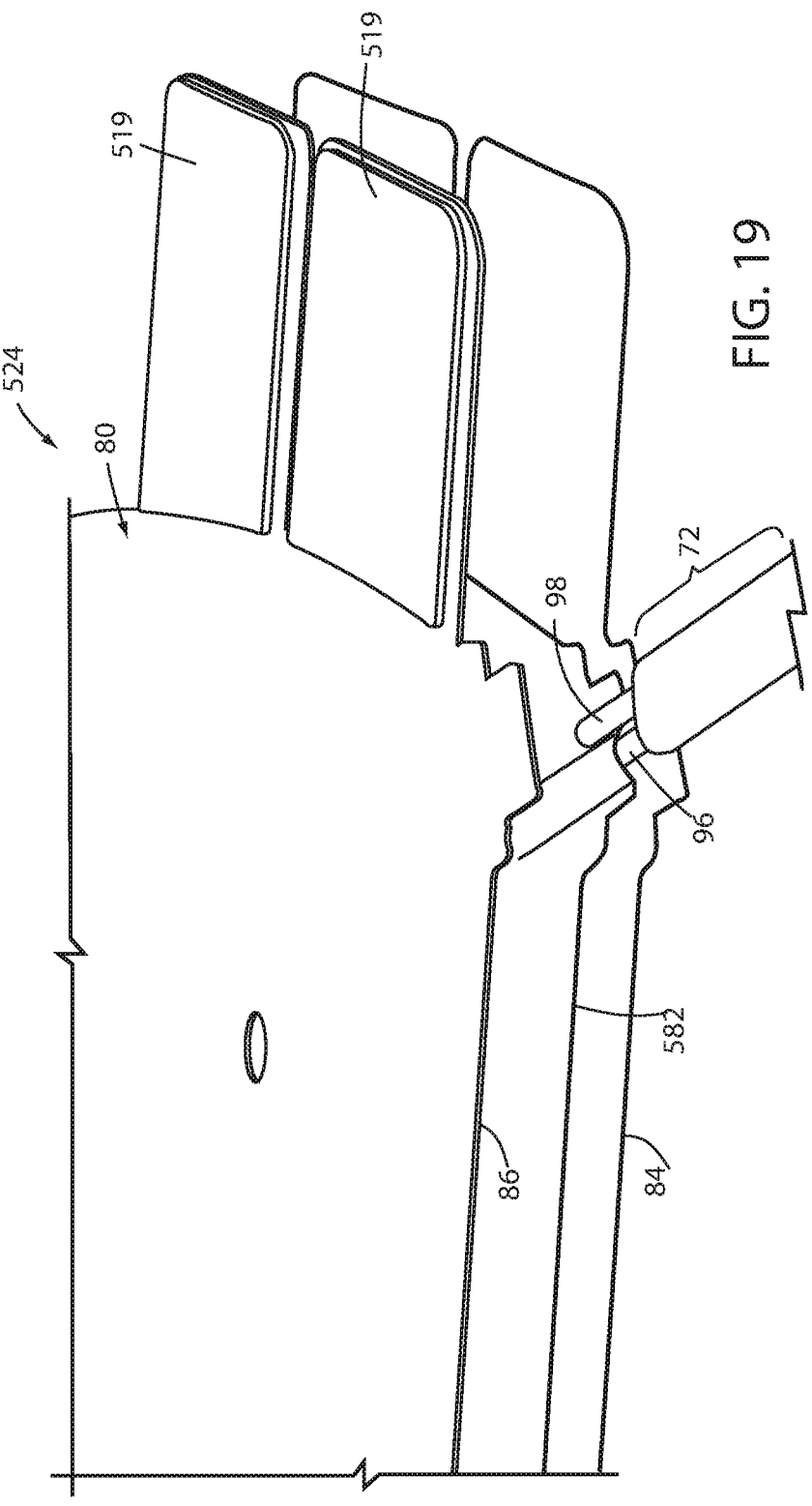
FIG. 18
FIG. 19

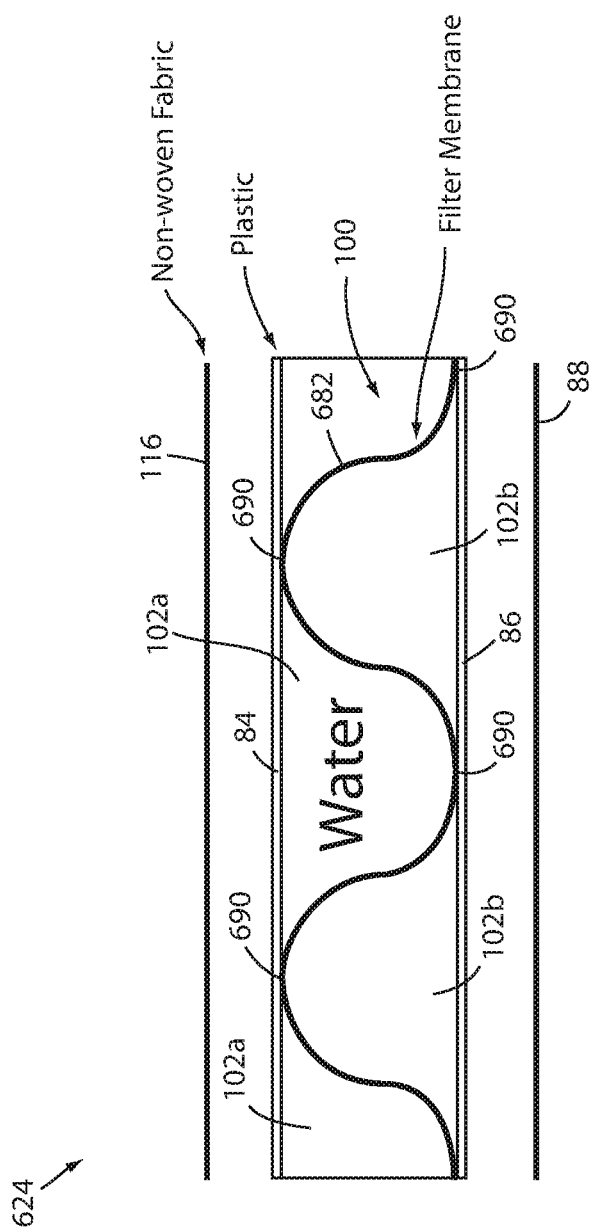

THERMAL SYSTEM WITH THERMAL PAD FILTERS

CROSS-REFERENCE TO RELATED APPLICATIONS

This application claims priority to U.S. patent application Ser. No. 16/710,065 filed Dec. 11, 2019, by inventors Andrew M. Bentz et al. and entitled THERMAL SYSTEM WITH THERMAL PAD FILTERS, which in turn claims priority to U.S. provisional patent application Ser. No. 62/778,034 filed Dec. 11, 2018, by inventors Andrew M. Bentz et al. and entitled THERMAL SYSTEM WITH THERMAL PAD FILTERS, the complete disclosures of both of which are incorporated herein by reference.

BACKGROUND

The present disclosure relates to a thermal control system for controlling the temperature of circulating fluid that is delivered to one or more thermal pads positioned in contact with a patient.

Thermal control systems are known in the art for controlling the temperature of a patient by providing a thermal control unit that supplies temperature controlled fluid to one or more thermal pads positioned in contact with a patient. The thermal control unit includes one or more heat exchangers for controlling the temperature of the fluid and a pump that pumps the temperature controlled fluid to the pad(s). The pads are placed in contact with the patient and facilitate the exchange of thermal energy between the patient and the fluid circulating through the pad, thereby either removing heat from the patient or supplying heat to the patient. After passing through the pad(s), the fluid is returned to the thermal control unit where any necessary adjustments to the temperature of the returning fluid are made before being pumped back to the pad(s). The thermal control unit and its coupled thermal pads can therefore be used to warm or cool a patient.

In one common arrangement, three pads are applied to the patient: one applied around the patient's torso, one applied around the patient's right leg, and one applied around the patient's left leg. The pads are often intended to be disposable such that, after use with a particular patient, they are discarded.

SUMMARY

The present disclosure provides various improved aspects to a thermal control system, including the thermal pads used with the thermal control system. In some embodiments, one or more fluid filters are integrated into the thermal pads to remove undesired matter from the fluid used with the thermal control system. The undesired matter includes, but it not limited to, bacteria and other microorganisms. By including the filters in disposable pads, fresh filters are automatically incorporated into the system whenever new thermal pads are used with the system (typically with every new patient), thereby allowing the thermal control system to be continuously filtered and automatically supplied with fresh filters without requiring a user to manually change such filters. Other improved aspects of the thermal control system are also disclosed herein and described in more detail below.

According to a first embodiment of the present disclosure, a thermal pad is provided that is adapted to be placed in physical contact with a patient and to receive temperature controlled fluid from a thermal control unit for controlling the patient's temperature. The thermal pad includes a first sheet, second sheet, peripheral seal, fluid inlet, fluid outlet, and a filter sheet. The first sheet is sheet adapted to face toward the patient and the second sheet is adapted to face away from the patient. The peripheral seal couples a periphery of the first sheet to a periphery of the second sheet to thereby define a fluid chamber between the first and second sheets. The fluid inlet and fluid outlet are in fluid communication with the fluid chamber and provide passageways for delivering fluid to, and receiving fluid out of, the fluid chamber. The filter sheet has a first surface facing toward the first sheet and a second surface facing toward the second sheet. The filter sheet is positioned within the fluid chamber such that fluid entering the fluid inlet must pass through the filter sheet before exiting out of the fluid outlet.

According to other aspects of the embodiment, the filter sheet, first sheet, and second sheet are all substantially parallel to each other. The filter sheet, second sheet, and first sheet all have a surface area of substantially the same magnitude, in some embodiments.

According to another aspect, the thermal pad includes a plurality of bonds wherein each of the bonds couples the first sheet, the second sheet and the filter sheet together.

In other embodiments, the first sheet and second sheet each have a surface area of substantially the same magnitude and the filter sheet has a surface area of a magnitude less than the magnitude of the first sheet and second sheet.

In at least one embodiment, the filter sheet is adapted to filter particles having a size of 0.2 microns or larger. In some such embodiments, a second filter sheet is also provided and is adapted to filter particles larger than 0.2 microns and to allow particles of 0.2 microns to pass therethrough.

In some embodiments, the first surface of the filter sheet is secured to the first sheet at a first plurality of locations and the second surface of the filter sheet is secured to the second sheet at a second plurality of locations that are different from the first plurality of locations.

A non-woven sheet positioned adjacent the first sheet and adapted to come into contact with the patient is provided in some embodiments. Either or both of the non-woven sheet and the first sheet are embedded with antimicrobial substances.

In still other embodiments, the filter sheet itself includes antimicrobial substances embedded therein that are adapted to come into contact with and kill microbes filtered by the filter sheet.

According to another embodiment of the present disclosure, a thermal pad is provided that is adapted to be placed in physical contact with a patient and to receive temperature controlled fluid for controlling the patient's temperature. The thermal pad includes a first sheet, second sheet, peripheral seal, fluid inlet, fluid outlet, a plurality of bonds, and a filter. The first sheet is adapted to face toward the patient and the second sheet is adapted to face away from the patient. The peripheral seal couples the periphery of the first sheet to a periphery of the second sheet to thereby define a fluid chamber between the first and second sheets. The fluid inlet and fluid outlet are in fluid communication with the fluid chamber and provide passageways for delivering fluid to, and receiving fluid out of, the fluid chamber. The plurality of bonds couple the first sheet, second sheet and filter sheet together. The filter is secured to the first sheet and the second sheet, and is positioned within the fluid chamber such that fluid entering the fluid inlet must pass through the filter sheet before exiting out of the fluid outlet.

According to other aspects, the thermal pad may also include a second filter and a third filter. When included, the second filter is positioned upstream of the filter and adapted to filter particles having a size of more than 0.2 microns and to allow particles of 0.2 microns to pass therethrough. The third filter is positioned downstream of the filter and adapted to filter particles having a size of more than 0.2 microns and to allow particles of 0.2 microns to pass therethrough.

In some embodiments, the filter defines a fluid channel that extends into the thermal pad. The channel may extend a distance into the thermal pad that is at least half of a length of the thermal pad or at least half of a width of the thermal pad. The filter may be bag shaped with an interior of the bag defining the fluid channel. In some embodiments, the bag shaped filter includes a top filter sheet and a bottom filter sheet and the plurality of bonds also bond the top filter sheet and the bottom filter sheet to each other and to the first sheet and second sheet.

According to another embodiment, a thermal pad is provided that is adapted to be placed in physical contact with a patient and to receive temperature controlled fluid from a thermal control unit for controlling the patient's temperature. The thermal pad includes a first sheet, second sheet, peripheral seal, fluid inlet, fluid outlet, and first, second, and third filters. The first sheet is sheet adapted to face toward the patient and the second sheet is adapted to face away from the patient. The peripheral seal couples a periphery of the first sheet to a periphery of the second sheet to thereby define a fluid chamber between the first and second sheets. The fluid inlet and fluid outlet are in fluid communication with the fluid chamber and provide passageways for delivering fluid to, and receiving fluid out of, the fluid chamber. The first, second, and third filters are all positioned in fluid communication with the fluid chamber. The third filter is also positioned between the first and second filters such that fluid flowing through the first filter must pass through the third filter before reaching the second filter. The first and second filters have a common pore rating for filtering particles of a first size, and the third filter has a pore rating for filtering particles of a second size. The second size is smaller than the first size.

According to other aspects of this embodiment, the third filter may have a pore rating for filtering particles having a size of 0.2 microns or larger and the first and second filters may have a pore rating for allowing particles having a size of greater than 0.2 microns to pass therethrough.

A non-woven sheet is provided in some embodiments that is positioned adjacent the first sheet and adapted to come into contact with the patient. The non-woven sheet is embedded with antimicrobial substances.

The third filter, in some embodiments, is a filter sheet comprising a first surface facing toward the first sheet and a second surface facing toward the second sheet. The filter sheet, first sheet, and second sheet are all substantially parallel to each other.

The first filter and the second filter, in some embodiments, define first and second channels that extend a distance into the thermal pad. The first filter and second filter may both be bag shaped, and the interior of the bag shaped filters defines the first and second channels, respectively.

According to another embodiment of the present disclosure, a thermal pad is provided that is adapted to be placed in physical contact with a patient and to receive temperature controlled fluid from a thermal control unit for controlling the patient's temperature. The thermal pad includes a first sheet, second sheet, peripheral seal, fluid inlet, fluid outlet, first connector, second connector, an inlet hose segment, an outlet hose segment, and a filter. The first sheet is sheet adapted to face toward the patient and the second sheet is adapted to face away from the patient. The peripheral seal couples a periphery of the first sheet to a periphery of the second sheet to thereby define a fluid chamber between the first and second sheets. The fluid inlet and fluid outlet are in fluid communication with the fluid chamber and provide passageways for delivering fluid to, and receiving fluid out of, the fluid chamber. The first connector is adapted to releasably couple to a supply hose from a thermal control unit. The second connector is adapted to releasably couple to a return hose of the thermal control unit. The inlet hose segment includes a first end coupled to the first connector and a second end coupled to the fluid inlet. The outlet hose segment includes a first end coupled to the second connector and a second end coupled to the fluid outlet. The filter is positioned inside of at least one of the inlet hose segment and the outlet hose segment such that temperature controlled fluid supplied from the thermal control unit is filtered as it passes through the filter pad.

According to other embodiments, the filter pad includes a second filter. In such embodiments, the filter is positioned in the inlet hose segment and the second filter is positioned in the outlet hose segment. In some embodiments, a third filter is positioned within the fluid chamber. The third filter may have a different pore rating than the filter and the second filter. The third filter may be a filter sheet coupled to the first and second sheets by a plurality of bonds.

Before the various embodiments disclosed herein are explained in detail, it is to be understood that the claims are not to be limited to the details of operation or to the details of construction, nor to the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 8 is a second alternative embodiment of a thermal pad usable with the thermal control system of FIG. 1;

FIG. 9 is a sectional view of the thermal pad of FIG. 8 taken along the IX-IX in FIG. 8;

FIG. 10 is a sectional view of the thermal pad of FIG. 8 taken along the line X-X in FIG. 8;

FIG. 11 is a plan view of a third alternative embodiment of a thermal pad usable with the thermal control system of FIG. 1;

FIG. 12 is a sectional view of the thermal pad of FIG. 11 taken along the line XII-XII in FIG. 11;

FIG. 13 is a sectional view of the thermal pad of FIG. 11 taken along the line XIII-XIII in

FIG. 11;

FIG. 14 is a plan view of a fourth alternative embodiment of a thermal pad usable with the thermal control system of FIG. 1;

FIG. 15 is a sectional view of the thermal pad of FIG. 14 taken along the line XV-XV in

FIG. 15;

FIG. 16 is a sectional view of the thermal pad of FIG. 14 taken along the line XVI-XVI in

FIG. 15;

FIG. 18 is a sectional view of the thermal pad of FIG. 17 taken along the line XVIII-XVIII in FIG. 17;

FIG. 19 is an exploded, partial perspective view of the thermal pad of FIG. 17; and FIG. 20 is a sectional view of a sixth alternative embodiment of a thermal pad usable with the thermal control system of FIG. 1.

DETAILED DESCRIPTION OF THE EMBODIMENTS

Figure 1:
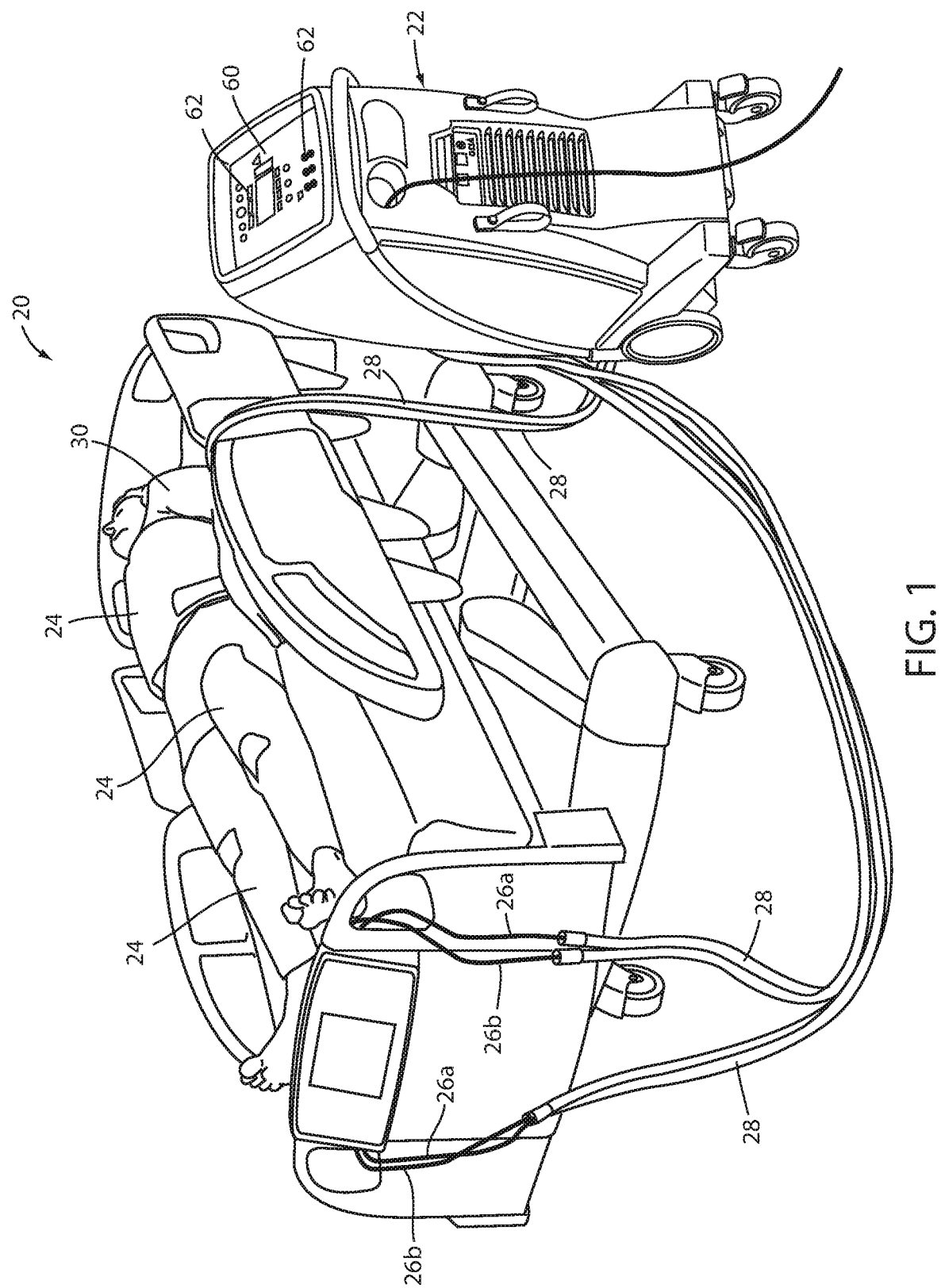
FIG. 1 is a perspective view of a thermal control system according to one aspect of the present disclosure shown applied to a patient on a patient support apparatus.

A thermal control system 20 according to one embodiment of the present disclosure is shown in FIG. 1. Thermal control system 20 is adapted to control the temperature of a patient 30. Such temperature control may involve raising, lowering, or maintaining the patient's temperature, or combinations thereof. Thermal control system 20 includes a thermal control unit 22 coupled to one or more thermal therapy devices 24. The thermal therapy devices 24 are illustrated in FIG. 1 to be thermal pads, but it will be understood that thermal therapy devices 24 may take on other forms, such as, but not limited to, blankets, vests, patches, caps, or other structure. For purposes of the following written description, thermal therapy devices 24 will be referred to as thermal pads 24, but it will be understood by those skilled in the art that this terminology is used merely for convenience and that the phrase "thermal pad" is intended to cover all of the different variations of thermal therapy devices 24 mentioned above (e.g. blankets, vests, patches, caps, etc.).

Thermal control unit 22 is coupled to thermal pads 24 via a plurality of hoses 26. Each thermal pad 24 includes a supply hose 26a and a return hose 26b. Thermal control unit 22 delivers temperature controlled fluid (such as, but not limited to, water) to the thermal pads 24 via the fluid supply hoses 26a. After the temperature controlled fluid has passed through thermal pads 24, thermal control unit 22 receives the temperature controlled fluid back from thermal pads 24 via the return hose 26b. In some modified embodiments of thermal control system 20, one or more auxiliary lines may be coupled between the thermal control unit 22 and one or more of the thermal pads. Such auxiliary lines may provide thermal control unit 22 with additional data regarding the patient, the thermal pads 24, and/or other information, or such auxiliary lines may provide a conduit for supplying a different fluid (e.g. a gas) to the thermal pads. Still other purposes may be served by the auxiliary line. Examples of the types of auxiliary lines that may be used in such modified thermal control systems are disclosed in the following commonly assigned U.S. patent applications: Ser. No. 15/675,061 filed Aug. 11, 2017, by inventors James K. Galer et al., and entitled THERMAL THERAPY DEVICES; Ser. No. 15/820,558 filed Nov. 22, 2017, by inventors Gregory S. Taylor et al. and entitled THERMAL SYSTEM; and Ser. No. 62/610,327 filed Dec. 26, 2017, by inventors Gregory S. Taylor et al. and entitled THERMAL SYSTEM WITH PATIENT SENSOR(S), the complete disclosures of all of which are incorporated herein in their entirety by reference. Still other types of auxiliary lines may be coupled between thermal control unit 22 and thermal pads 24.

In the embodiment of thermal control system 20 shown in FIG. 1, three thermal pads 24 are used in the treatment of patient 30. A first thermal pad 24 is wrapped around a patient's torso, while second and third thermal pads 24 are wrapped, respectively, around the patient's right and left legs. Other configurations can be used and different numbers of thermal pads 24 may be used with thermal control unit 22, depending upon the number of inlet and outlet ports that are included with thermal control unit 22. By controlling the temperature of the fluid delivered to thermal pads 24 via supply hoses 26a, the temperature of the patient 30 can be controlled via the close contact of the pads 24 with the patient 30 and the resultant heat transfer therebetween.

In some embodiments, such as that shown in FIG. 1, one or more of the hoses 26 may be partially or wholly enveloped in a thermal covering 28 in order to help prevent heat transfer between the fluid inside the hoses 26 and the surrounding ambient air. The thermal covering 28 may be made from any suitably flexible material having good thermal resistance.

Figure 2:
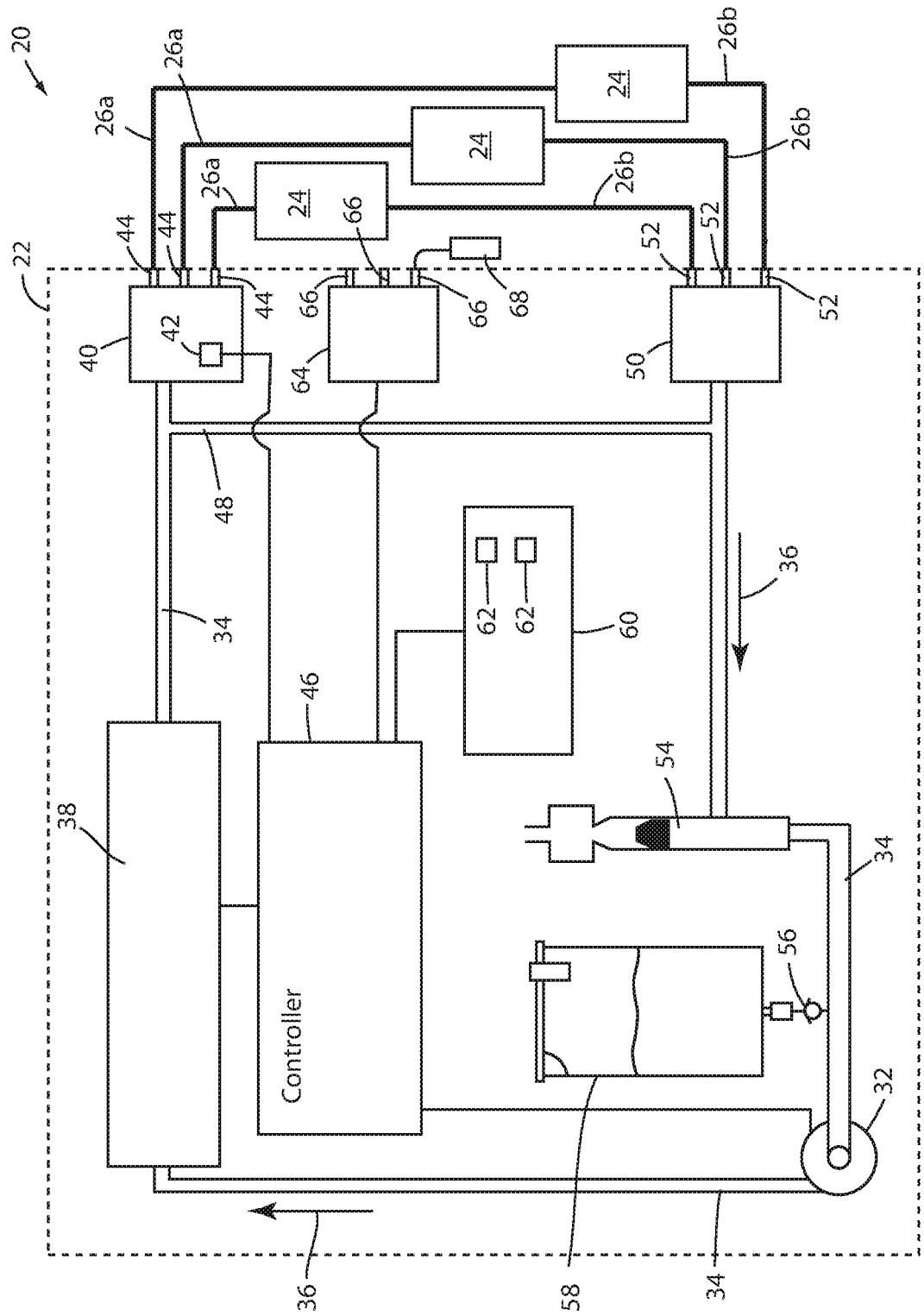
FIG. 2 is a block diagram of the thermal control system of FIG. 1 showing further internal details of one example of a thermal control unit usable with the thermal control system of FIG. 1.

Thermal control unit 22 is adapted to raise or lower the temperature of the fluid supplied to thermal pads 24 via supply hoses 26a. As shown in FIG. 2, thermal control unit 22 includes a pump 32 for circulating fluid through a circulation channel 34. Pump 32, when activated, circulates the fluid through circulation channel 34 in the direction of arrows 36 (clockwise in FIG. 2). Starting at pump 32 the circulating fluid first passes through a heat exchanger 38 where it is delivered to an outlet manifold 40 having an outlet temperature sensor 42 and a plurality of outlet ports 44. Outlet ports 44 are adapted to fluidly couple to supply and return hoses 26a and 26b. In some embodiments, a plurality of valves (not shown) may also be included within outlet manifold 40 in order to individually control the amount of fluid exiting those ports 44 that are coupled to supply hoses 26a, thereby allowing the thermal control unit 22 to individually control how much fluid flows to each of the pads 24. In other embodiments, such valves are omitted. Although FIG. 2 illustrates three outlet ports 44, it will be understood that this number may vary.

Temperature sensor 42 is adapted to detect a temperature of the fluid inside of outlet manifold 40 and report it to a controller 46. As will be discussed more below, controller 46 uses this temperature reading as feedback for the control of heat exchanger 38. Thermal control unit 22 also includes a bypass line 48 fluidly coupled to outlet manifold 40 and an inlet manifold 50. Bypass line 48 allows fluid to circulate through circulation channel 34 in a complete circuit even in the absence of any thermal pads 24 or hoses 26a being coupled to any of outlet ports 44. That is, bypass line 48 allows fluid to flow from heat exchanger 38 to inlet manifold 50. From inlet manifold 50, the fluid is able to flow back to pump 32, which is fluidly coupled thereto by circulation channel 34. The fluid is therefore able to make a complete circuit within thermal control unit 22. In some embodiments, bypass line 48 includes a valve used to control when and how much fluid is allowed to flow through bypass line 48. The valve, if included, may be a pressure operated valve that responds to the fluid pressure, or it may be a valve controlled by controller 46.

Inlet manifold 50 includes a plurality of inlet ports 52 (the precise number may vary from the three illustrated in FIG. 2) that couple to return hoses 26b and receive fluid returning from the one or more connected thermal pads 24. The incoming fluid from inlet ports 52, as well as the fluid passing through bypass line 48, travels back toward the pump 32 into an air separator 54. Air separator 54 includes any structure in which the flow of fluid slows down sufficiently to allow air bubbles contained within the circulating fluid to float upwardly and escape to the ambient surrounding. In some embodiments, air separator 54 is constructed in accordance with any of the configurations disclosed in commonly assigned U.S. patent application Ser. No. 15/646,847 filed Jul. 11, 2017, by inventor Gregory S. Taylor and entitled THERMAL CONTROL SYSTEM, the complete disclosure of which is hereby incorporated herein by reference. After passing through air separator 54, the circulating fluid flows past a valve 56 positioned beneath a fluid reservoir 58 that supplies fluid to thermal control unit 22. After passing by valve 56, the circulating fluid travels to pump 32 and the circuit is repeated.

Controller 46 of thermal control unit 22 is contained within a main body of thermal control unit 22 and is in electrical communication with a variety of different sensors and/or actuators. More specifically, controller 46 is in electrical communication with pump 32, heat exchanger 38, outlet temperature sensor 42, and a control panel 60 (FIGS. 1 & 2). Control panel 60 includes a plurality of controls 62 that allow a user to operate thermal control unit 22, including setting a desired fluid target temperature and/or a desired patient target temperature, and/or to control other aspects of thermal control unit 22. Control panel 60 communicates with controller 46 and includes controls enabling a user to turn control unit 22 on and off, as well as one or more controls enabling the user to select a target temperature for the fluid delivered to thermal pads 24. In some embodiments, control panel 60 also allows a user to select from different modes for controlling the patient's temperature. One of the modes includes a manual mode in which the user selects a target temperature for the fluid. Control unit 22 then makes adjustments to heat exchanger 38 in order to ensure that the temperature of the fluid exiting supply hoses 26a is at the user-selected temperature.

Another one of the modes is an automatic mode. When the user selects the automatic mode, the user selects a target patient temperature, rather than a target fluid temperature. After selecting the target patient temperature, controller 46 makes automatic adjustments to the temperature of the fluid in order to bring the patient's temperature to the desired patient target temperature. In this mode, the temperature of the circulating fluid may vary as necessary in order to bring about the target patient temperature. Both the manual and automatic modes can be used for cooling and heating the patient.

In some embodiments, when the user selects the automatic mode, the thermal control unit 22 is configured to allow the user to select one or more desired heating or cooling rates for use in the automatic mode. When such rates are selected by the user, thermal control unit 22 not only brings the patient to the target patient temperature, but does so at the rate specified by the user. Still other variables, such as the maximum difference between the patient's temperature and the fluid temperature, may also be selected by the user using control panel 60, in at least some embodiments.

Control panel 60 may take on a wide variety of different forms. In some embodiments, control panel 60 may include any of the features and functionality of the control panel 46 disclosed in commonly assigned U.S. patent application Ser. No. 14/282,383 filed May 20, 2014, by inventors Christopher J. Hopper et al. and entitled THERMAL CONTROL SYSTEM, the complete disclosure of which is incorporated herein by reference. Additionally, or alternatively, control panel 60 may include any of the features and/or functionality of the user interface 76 and/or display 80 disclosed in commonly assigned U.S. patent application Ser. No. 62/610,362 filed Dec. 26, 2017, by inventor Gregory S. Taylor and entitled THERMAL SYSTEM WITH GRAPHICAL USER INTERFACE, the complete disclosure of which is also incorporated herein by reference. Still further, control panel 60 may include one or more controls 62 for implementing a pause/event control, a medication control, and/or an automatic temperature adjustment control, wherein these controls operate in accordance with the pause event control 66b, medication control 66c, and automatic temperature adjustment control 66d disclosed in commonly assigned U.S. patent application Ser. No. 62/577,772 filed on Oct. 27, 2017, by inventors Gregory Taylor et al. and entitled THERMAL SYSTEM WITH MEDICATION INTERACTION, the complete disclosure of which is also incorporated herein by reference. Such controls may be activated as touch screen controls or dedicated controls.

Controller 46 includes any and all electrical circuitry and components necessary to carry out the functions and algorithms described herein, as would be known to one of ordinary skill in the art. Generally speaking, controller 46 may include one or more microcontrollers, microprocessors, and/or other programmable electronics that are programmed to carry out the functions described herein. It will be understood that controller 46 may also include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions in thermal control unit 22, or they may reside in a common location within thermal control unit 22. When physically distributed, the components may communicate using any suitable serial or parallel communication protocol, such as, but not limited to, CAN, LIN, Firewire, I-squared-C, RS-232, RS-485, universal serial bus (USB), etc.

When operating in the automatic mode, thermal control unit 22 utilizes a patient temperature module 64 (FIG. 2). Patient temperature module 64 includes one or more patient temperature sensor ports 66 that are adapted to receive one or more conventional patient temperature sensors or probes 68. The patient temperature probes 68 may be any suitable patient temperature sensor that is able to sense the temperature of the patient at the location of the sensor. In one embodiment, the patient temperature sensors are conventional Y.S.I. 400 probes marketed by YSI Incorporated of Yellow Springs, Ohio, or probes that are YSI 400 compliant. In other embodiments, different types of sensors may be used with thermal control unit 22. Regardless of the specific type of patient temperature sensor used in thermal control system 20, each temperature probe 68 is connected to a patient temperature sensor port 66 positioned on thermal control unit 22. Patient temperature sensor ports 66 are in electrical communication with controller 46 and provide current temperature readings of the patient's temperature.

Controller 46, in some embodiments, controls the temperature of the circulating fluid using closed-loop feedback from temperature sensor 42. That is, controller 46 determines (or receives) a target temperature of the fluid, compares it to the measured temperature from sensor 42, and issues a command to heat exchanger 38 that seeks to decrease the difference between the desired fluid temperature and the measured fluid temperature. In some embodiments, the difference between the fluid target temperature and the measured fluid temperature is used as an error value that is input into a conventional Proportional, Integral, Derivative (PID) control loop. That is, controller 46 multiplies the fluid temperature error by a proportional constant, determines the derivative of the fluid temperature error over time and multiplies it by a derivative constant, and determines the integral of the fluid temperature error over time and multiplies it by an integral constant. The results of each product are summed together and converted to a heating/cooling command that is fed to heat exchanger 38 and tells heat exchanger 38 whether to heat and/or cool the circulating fluid and how much heating/cooling power to use.

When thermal control unit 22 is operating in the automatic mode, controller 46 may use a second closed-loop control loop that determines the difference between a patient target temperature and a measured patient temperature. The patient target temperature is input by a user of thermal control unit 22 using control panel 60. The measured patient temperature comes from a patient temperature probe 68 coupled to one of patient temperature sensor ports 66 (FIG. 2). Controller 46 determines the difference between the patient target temperature and the measured patient temperature and, in some embodiments, uses the resulting patient temperature error value as an input into a conventional PID control loop. As part of the PID loop, controller 46 multiplies the patient temperature error by a proportional constant, multiplies a derivative of the patient temperature error over time by a derivative constant, and multiplies an integral of the patient temperature error over time by an integral constant. The three products are summed together and converted to a target fluid temperature value. The target fluid temperature value is then fed to the first control loop discussed above, which uses it to compute a fluid temperature error.

It will be understood by those skilled in the art that other types of control loops may be used. For example, controller 46 may utilize one or more PI loops, PD loops, and/or other types of control equations. In some embodiments, the coefficients used with the control loops may be varied by controller 46 depending upon the patient's temperature reaction to the thermal therapy, among other factors. One example of such dynamic control loop coefficients is disclosed in commonly assigned U.S. patent application Ser. No. 62/577,772 filed on Oct. 27, 2017, by inventors Gregory Taylor et al. and entitled THERMAL SYSTEM WITH MEDICATION INTERACTION, the complete disclosure of which is incorporated herein by reference.

Regardless of the specific control loop utilized, controller 46 implements the loop(s) multiple times a second in at least one embodiment, although it will be understood that this rate may be varied widely. After controller 46 has output a heat/cool command to heat exchanger 38, controller 46 takes another patient temperature reading (from probe 68) and/or another fluid temperature reading (from sensor 42) and re-performs the loop(s). The specific loop(s) used, as noted previously, depends upon whether thermal control unit 22 is operating in the manual mode or automatic mode.

It will also be understood by those skilled in the art that the output of any control loop used by thermal control unit 22 may be limited such that the temperature of the fluid delivered to thermal pads 24 never strays outside of a predefined maximum or a predefined minimum. The predefined maximum and minimum are used in order to ensure patient safety and to avoid delivering fluid that is either too hot or too cold for patient safety.

Control unit 22 may also be modified to include one or more flow sensors that measure the rate of fluid flow and report this information to controller 46. In such modified embodiments, controller 46 uses the flow rate in determining what control signals to send to heat exchanger 38 and/or pump 32.

It will be understood by those skilled in the art that the particular order of the components along circulation channel 34 of control unit 22 may be varied from what is shown in FIG. 2. For example, although FIG. 2 depicts pump 32 as being upstream of heat exchanger 38 and air separator 54 as being downstream of heat exchanger 38, this order may be changed. Air separator 54, pump 32, heat exchanger 38 and reservoir 58 may be positioned at any suitable location along circulation channel 34. Indeed, in some embodiments, reservoir 58 is moved so as to be in line with and part of circulation channel 34, rather than external to circulation channel 34 as shown in FIG. 2, thereby forcing the circulating fluid to flow through reservoir 58 rather than around reservoir 58.

Still further, in some embodiments, circulation channel 34 may be modified so as to allow controller 46 to selectively move reservoir 58 into, and out of, circulation channel 34. Such modifications may include the addition of a reservoir valve (not shown) between air separator 54 and valve 56. When the reservoir valve is open, fluid from air separator 54 flows along circulation channel 34 to pump 32 without passing through reservoir 58. When the reservoir valve is closed, fluid coming from air separator 54 is diverting along a channel that leads into reservoir 58. Fluid inside of reservoir 58 then flows back into circulation channel 34 via valve 56. Once back in circulation channel 34, the fluid flows to pump 32 and is pumped to the rest of circulation channel 34 and thermal pads 24 and/or bypass line 48. Controller 46 may control the reservoir valve in order to bring about quicker changes in the temperature of the circulating fluid, and may do so through the use of a reservoir temperature sensor that senses the temperature of the fluid inside of reservoir 58. Further details of one manner of implementing such a reservoir valve, as well as controlling it in order to effectuate rapid fluid temperature changes, are disclosed in commonly assigned U.S. patent application Ser. No. 62/610,319 filed Dec. 26, 2017, by inventors Gregory S. Taylor et al. and entitled THERMAL SYSTEM WITH OVERSHOOT REDUCTION, the complete disclosure of which is incorporated herein by reference.

Figure 3:
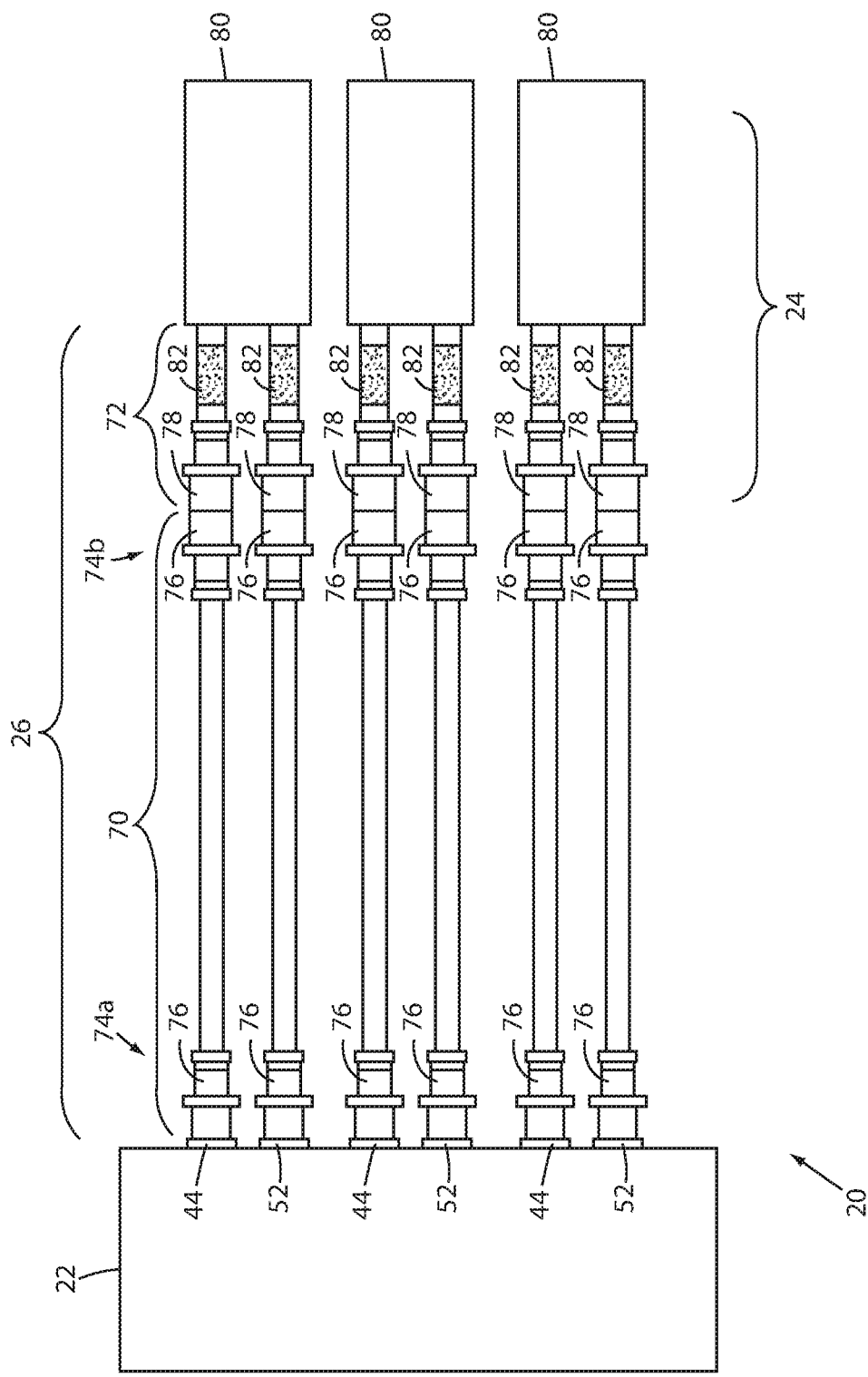
FIG. 3 is another block diagram of the thermal control system of FIG. 1 showing further details of the hose constructions of a first set of thermal pads that are usable with the thermal control system.

FIG. 3 illustrates in greater detail the coupling of hoses 26 between thermal control unit 22 and thermal pads 24. As shown therein, each hose 26 is comprised of an intermediate segment 70 and a thermal pad segment 72. Each intermediate hose segment 70 includes two ends 74a and 74b. A connector 76 is coupled to each end 74a and 74b. Connectors 76 are adapted to releasably couple intermediate hose segment 70 to other structures. Specifically, connectors 76 on first end 74a of intermediate hose segments 70 are adapted to releasably couple to outlet ports 44 and inlet ports 52 of thermal control unit 22. Connectors 76 on second end 74b of intermediate hose segments 70 are adapted to releasably couple to mating connectors 78 that are integrated with thermal pad hose segments 72.

Connectors 78 of thermal pads 24 are integrally coupled to thermal pad hose segments 72. That is, connectors 78 are not able to be decoupled from thermal pad hose segments 72 without damaging hose segment 72. Similarly, thermal pad hose segments 72 are integrally coupled to a main body portion 80 of thermal pads 24. Such hose segments 72 cannot be decoupled from the thermal pad body portions 80 without damaging the thermal pad 24. Connectors 76 and 78 may be any suitable commercially available connector that allows hose segments 70 and 72 to be easily fluidly coupled and decoupled. In some embodiments, connectors 76 and 78 may be what is commonly referred to as "Colder style" connectors. Other types of connectors, however, can be used.

In practice, intermediate hose segments 70 are typically not disposable, but instead are re-used from patient to patient. Thermal pad hose segments 72, however, are typically discarded after a patient's treatment has finished. This is because thermal pads 24 are typically discarded after use with a single patient, and thermal pad hose segments 72 are an integral part of the thermal pads 24. Consequently, whenever thermal control system 20 is used with a new patient, the new patient typically has his or her torso and legs wrapped with a new set of thermal pads 24.

In the embodiment of thermal pads 24 shown in FIG. 3, each thermal pad 24 includes a filter 82 positioned inside of each of the thermal pad hose segments 72. Filters 82 are adapted to filter particles from the fluid circulating to and from thermal pads 24, which is typically water, although it will be understood that other liquids may be used, including non-water based mixtures. The particles filtered by filters 82 include, but are not limited to, microbes and other potentially infectious agents. In some embodiments, filters 82 have pore sizes of 0.2 microns such that the majority of particles passing therethrough are smaller than 0.2 microns in size. In other embodiments, filters 82 may have different port sizes.

In the embodiment shown in FIG. 3, each thermal pad includes two filters 82 positioned in both of the thermal pad hose segments 72 of each thermal pad 24. It will be understood that this may be modified in a number of different manners. For example, in some modified embodiments of thermal pad 24, only a single one of the hose segments 72 of each thermal pad 24 includes a filter 82. This single filter may be positioned in either the inlet hose segment 72 or the outlet hose segment 72 of the thermal pad 24. In another modified embodiment, one or more additional filters 82 are included within the main body portion 80 of thermal pad 24. The inclusion of one or more additional fluid filters 82 within main body portion 80 may be implemented where both hose segments 72 (inlet and outlet) of thermal pad 24 include a filter 82, or it may be implemented where only a single one of hose segments 72 (inlet or outlet) of thermal pad 24 include a filter 82.

In still other embodiments, thermal control system 20 may be modified to include one or more filters 82 positioned inside of one or both of the intermediate hose segments 70 that coupled to a particular thermal pad 24. Such filters 82 may be in lieu of, or in addition to, any filters 82 that are positioned inside of the main body 80 of thermal pads 24 and/or inside thermal pad hose segments 72. However, it will be understood that positioning filters 82 inside of thermal pad segments 72 and/or the main bodies 80 of thermal pads 24, rather than intermediate hose segments 70, has the advantage that the filters 82 are then disposed of whenever a new thermal pad 24 is used with system 20. This relieves the user of thermal control system 20 of having to perform the separate job of changing a filter.

It will be understood by those skilled in the art that the use of filters 82 in thermal pads 24 (hose segments 72 and/or main bodies 80) allows thermal control unit 22 to be constructed without any internal filters, thereby relieving the user of the need to change or replace filters within thermal control unit 22. Instead, fresh filters 82 are automatically provided whenever a new patient is used with thermal control system 20 who receives a new set of thermal pads 24.

In still another modified embodiment of thermal control system, thermal control unit 22 includes an internal fluid filter 82 and thermal pads 24 also include one or more fluid filters (located in main body 80 and/or hose segments 72). In this embodiment, thermal control unit 22 includes a filter 82 that has a smaller pore size than the filters 82 included within the thermal pads 24. The larger pore size of the filters 82 in the thermal pads 24 removes the larger particles from the fluid, thereby helping to prevent the smaller pore sized filter 82 within thermal control unit 22 from becoming clogged. This tends to prolong the life of the smaller pore sized filter 82 contained within thermal control unit 22, thereby reducing the frequency at which the smaller pore-sized filter 82 within thermal control unit 22 needs to be replaced. Further, because smaller pore sized filters tend to more expensive than larger pore sized filters, this arrangement prolongs the life of the more expensive filter 82 within thermal control unit 22 while causing the less expensive filters 82 within the thermal pads 24 to be discarded. The use of less expensive filters 82 within thermal pads 24, of course, also tends to reduce the price of the thermal pads 24 relative to comparable thermal pads 24 having smaller pore sized filters.

In the aforementioned embodiment of thermal control system 20 where thermal control unit 22 includes a smaller pore sized filter 82 than the filters 82 within thermal pads 24, it may be advantageous to locate the smaller pore sized filter 82 within inlet manifold 50, or between inlet manifold 50 and the downstream end of bypass line 48. By selecting one of these locations, the internal filter 82 within thermal control unit 22 only receives and filters liquid that has already passed through thermal pads 24 and their associated filters 82. The internal filter 82 within thermal control unit 22 therefore only filters liquid that has been pre-filtered by the larger pore filters 82 of thermal pads 24. These larger pore filters 82 remove most of the larger particles from the fluid traveling through the internal filter 82, thereby prolonging the life of the relatively more expensive filter 82 that is internal to thermal control unit 22.

Figure 4:
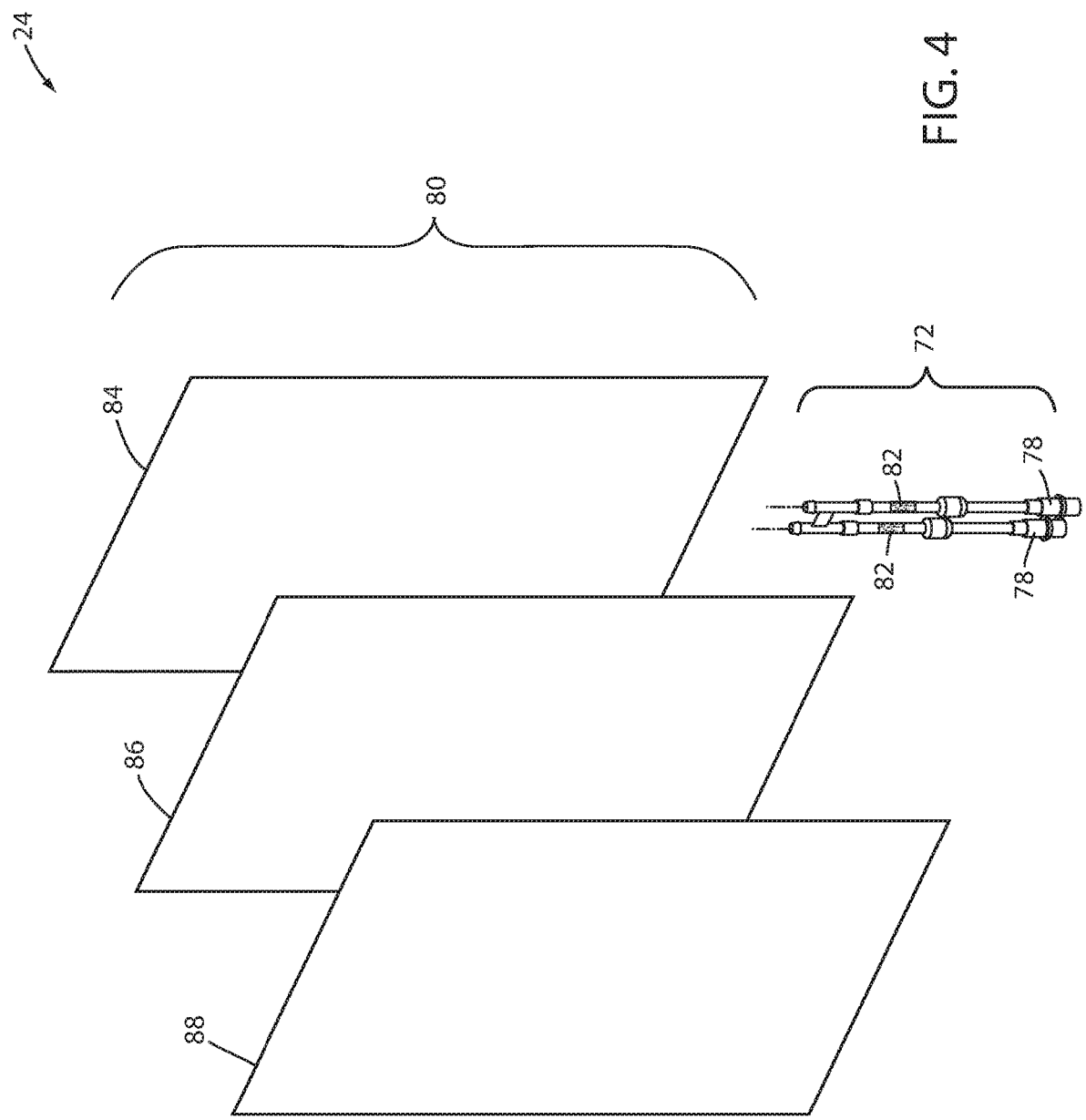
FIG. 4 is an exploded view of one of the thermal pads of FIG. 3.

FIG. 4 illustrates in greater detail one manner of constructing thermal pads 24. As shown therein, main body portion 80 of thermal pad 24 includes a first sheet 84, a second sheet 86, and an insulating sheet 88. First sheet 84 is adapted to face toward a patient and, in some instances, be placed in physical contact with the patient when undergoing thermal therapy. Second sheet 86 is adapted to face away from the patient during thermal therapy. Insulating sheet 88 is an optional sheet that, when included, is adapted retard the flow of thermal energy between the fluid circulating within main body 80 of thermal pad 24 and its ambient surroundings.

First sheet 84 and second sheet 86 may be constructed from a variety of different materials. In some embodiments, first and second sheets 84 and 86 are constructed from a polyester and/or nylon composite. Other materials that are suitably flexible to allow sheets 84 and 86 to be wrapped around a patient and that have relatively good thermal conductivity, however, may be used. Insulation sheet 88 may be constructed from any suitably flexible material that has relatively poor thermal conductivity properties so as to thermally insulate the other sheets (and the fluid contained therein) from the temperature of the ambient surroundings. In some embodiments, insulation sheet 88 is constructed from material that includes a polyester foam, or other type of foam. Still other constructions are possible.

First and second sheets 84 and 86 are bonded to each other by a peripheral seal 87 that extends about their respective peripheries. Such bonding may be accomplished in any suitable manner provided the bonding forms a liquid impermeable bond. In some embodiments, the bonding is carried out using welds. Such welds may be implemented via heat welding, ultrasonic welding, Radio Frequency (RF) welding, or by other types of welding. In addition to being bonded to each other around their perimeters, first and second sheets 84 and 86 are bonded to each other at a plurality of internal locations 90 (not visible in FIG. 4, but shown in FIG. 5) (FIG. 4). Such bonding may also be carried out in any suitably manner, including by use of one or more of the welding techniques mentioned above. The space between first and second sheets 84 and 86 where they are not bonded to each other defines a fluid chamber in which the temperature controlled fluid supplied by thermal control unit 22 (via supply hose 26a) circulates.

In some regions of thermal pad 24, the bonding locations 90 are contiguous with each other to create one or more fluid passageway walls (not shown) within thermal pad 24. Such walls guide the fluid as it circulating within the main body portion 80 of thermal pads 24. In some embodiments, one or more of such walls may be included that divide thermal pad 24 into one or more fluidly isolated zones, such as disclosed in commonly assigned U.S. patent application Ser. No. 62/373,564 filed Aug. 11, 2016, by inventors James Galer et al. and entitled THERMAL SYSTEM, the complete disclosure of which is incorporated herein by reference.

In some embodiments, first sheet 84 may be comprised of, or have attached to it, a gel layer that is adapted to releasably adhere to the skin of the patient and thereby maintain contact with the patient's skin during the course of thermal therapy. The particular gel material used may vary. In some embodiments, the gel is a urethane gel. The specific chemical composition of the urethane gel can be adjusted to change the adhesive properties of the side of sheet 84 that contacts the patient's skin. When first sheet 84 includes gel, it may be secured thereto by RF welding, lamination, by being poured thereon, or by other means. Regardless of the specific gel used and the specific manner it is secured to first sheet 84, the gel should provide suitable adhesion to the surface of the patient's skin in order to resist physical separation between the pad 24 and the patient, yet not be so resistant to physical separation so as to cause discomfort to the patient when the pad 24 is subsequently removed.

In some embodiments, thermal pad 24 is modified to include additional sheets or layers beyond those shown in FIG. 4. When such additional layers are included, multiple fluid chambers may be defined within a thermal pad 24. Examples of such multi-chamber thermal pads are disclosed in commonly assigned U.S. patent application Ser. No. 62/373,658 filed Aug. 11, 2016, by inventors James Galer et al. and entitled THERMAL THERAPY DEVICES, the complete disclosure of which is incorporated herein.

Although not shown, thermal pad 24 may also include one or more straps that are used to secure thermal pad 24 to patient 30 when in use. Each strap may be adapted to releasably attach to another strap after thermal pad 24 has been wrapped around the patient 30. In some embodiments, the straps include hook and loop type fasteners, such as those sold under the tradename Velcro, while in other embodiments, the straps include one or more repositionable tapes. In other embodiments, the straps include other types of fasteners for securing themselves to each other in order to maintain pad 24 in a wrapped stated around the patient's leg or torso.

Although thermal pads 24 are depicted in FIGS. 3 and 4 as having generally rectangular shapes, it will be understood by those skilled in the art that this may be varied greatly. That is, thermal pad 24 may take on any shape that is conducive to being wrapped around one or more portions of patient 30. In some embodiments, those thermal pads 24 that are intended to be wrapped around the patient's torso have a different shape than those intended to be wrapped around the patient's legs. Those adapted to be wrapped around the patient's legs may include one or more cutouts or contours that allow the patient to bend his or her knees while thermal pads 24 are wrapped around his or her legs.

Figure 5:
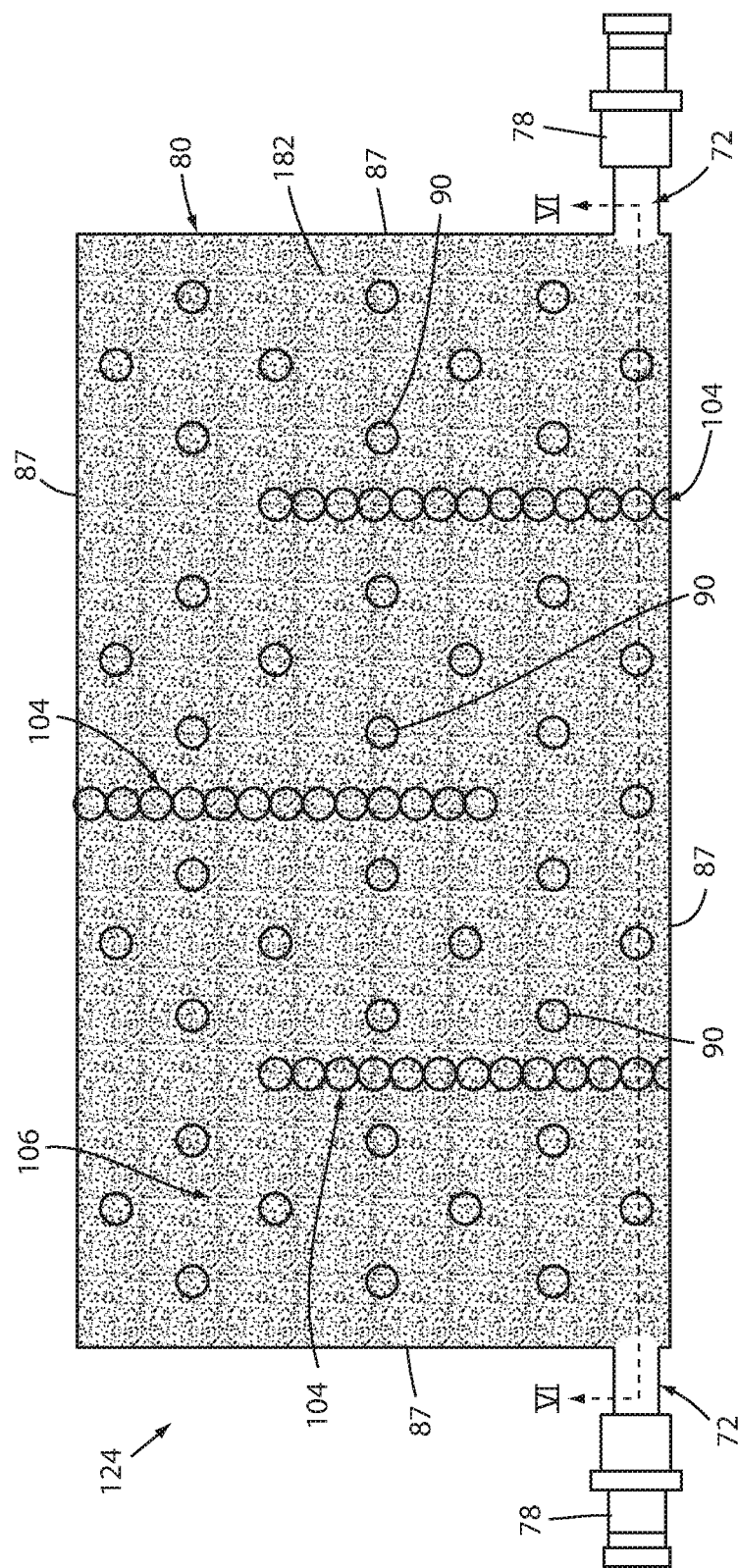
FIG. 5 is a plan view of a first alternative embodiment of a thermal pad usable with the thermal control system of FIG. 1.
Figure 6:
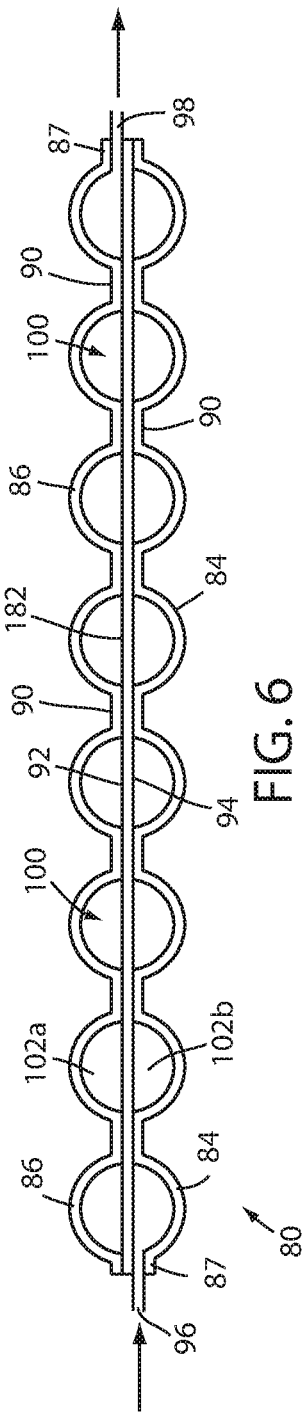
FIG. 6 is a sectional view of the thermal pad of FIG. 5 taken along the line VI-VI in FIG. 5.

FIGS. 5 and 6 illustrate an alternative embodiment of a thermal pad 124 that may be used with thermal control system 20 in place of one or more of thermal pads 24. Thermal pad 124 includes a number of components that are common to thermal pads 24 and those components are provided with the same reference number. Unless otherwise stated explicitly below, the common components are constructed and operate in the same manner previously described, serve the same functions previously described, and may be modified in any one or more of the previously described manners. Thermal pad 124 also includes one or more components that are similar to components of thermal pad 24 but modified in some manner. Such modified components are labeled with the same reference number increased by one hundred. Those components of thermal pad 124 that are not found in thermal pad 24 and/or that were not previously described or assigned a reference number are provided with a new reference number.

Thermal pad 124 differs from thermal pad 24 primarily in the location of its filter (FIGS. 5-6). More specifically, thermal pad 124 includes a filter 182 positioned inside of main body 80 and no filters included within hose segments 72. Filter 182 is a generally flat sheet that is sandwiched between first sheet 84 and second sheet 86. Filter sheet 182 is secured to first and second sheets 84 and 86 about its periphery, as well as at bonding locations 90. An interior fluid chamber 100 is defined between the first and second sheets 84 and 86 in those locations where first and second sheets 84 and 86 are not bonded together. Filter sheet 182 essentially divides fluid chamber 100 into two halves: an upper half 102a and a lower half 102b. Filter sheet 182 includes a top surface 92 that faces toward second sheet 86 and a bottom surface 94 that faces toward first sheet 84. Upper half 102a of fluid chamber 100 is defined between top surface 92 of filter sheet 182 and the interior side of second sheet 86. Lower half 102b of fluid chamber 100 is defined between bottom surface 94 of filter sheet 192 and the interior side of first sheet 84.

Filter sheet 182 is arranged such that fluid entering an inlet 96 (e.g. a first one of hose segments 72) enters lower half 102b of fluid chamber 100 and fluid exiting an outlet 98 (e.g. a second one of the hose segments 72) exits out of the upper half 102a of fluid chamber 100. Accordingly, in order for fluid entering inlet 96 to exit out of outlet 98, the fluid must pass from lower half 102b through filter sheet 182 to upper half 102a. Filter sheet 182 therefore filters all water passing through thermal pad 124. Filter 182, in some embodiments, is made of a material that stretches in response to the fluid pressure less than the material of first and second sheets 84 and 86. The fluid pressure therefore does not stretch filter 182 such that it abuts against first or second sheet 84 or 86, but instead allows filter 182 to remain generally spaced apart from both sheets 84 and 86 (at locations other than bonding locations 90 and its peripheral seal).

By utilizing a filter sheet 182 having a surface area substantially equal to the planar footprint of first and second sheets 84 and 86, filter sheet 182 is able to provide a filtering surface having a significantly large surface area, thereby allowing fluid to pass therethrough at a large number of locations, and thereby also extending the life of the filter when compared to a filter having a smaller surface area.

Thermal pad 124 includes a number of interior walls 104 that define a plurality of fluid passageways 106. In the embodiment shown in FIG. 5, walls 104 are defined by a series of bonding locations 90 that are contiguous with each other. It will be understood that walls 104 may be arranged in any suitable manner and that the particular arrangement shown in FIG. 5 is but one arbitrary example of such an arrangement. Temperature controlled fluid supplied to thermal pad 124 via inlet 96 (which couples to a fluid supply hose 26a of thermal control unit 22) flows into a passageway 106 that follows a tortuous path to outlet 98. With reference to the orientation of main body 80 as depicted in FIG. 6, passageway 106 extends up and down past a series of three walls 104 before terminating at a corner of main body 80 adjacent outlet 98. The inclusion of one or more passageways 106 within main body 80 helps to ensure that the fluid delivered to thermal pad 24 is circulated throughout the entire interior of thermal pad 24 before being returned to thermal control unit 22.

It will be understood by those skilled in the art that the particular orientation of thermal pad 124 shown in FIG. 6 and the descriptors used herein to describe that orientation (e.g. "upper" and "lower") are arbitrary. That is, for example, although FIG. 6 depicts inlet 96 entering into lower half 102b of fluid chamber 100, thermal pad 124 could be modified to have inlet 96 enter into upper half 102a and exit out of lower half 102b. It will also be appreciated that thermal pad 124 can be modified to include additional layers, such as, but not limited to, a nonwoven insulation sheet 88 and/or one or more other layers.

Figure 7:
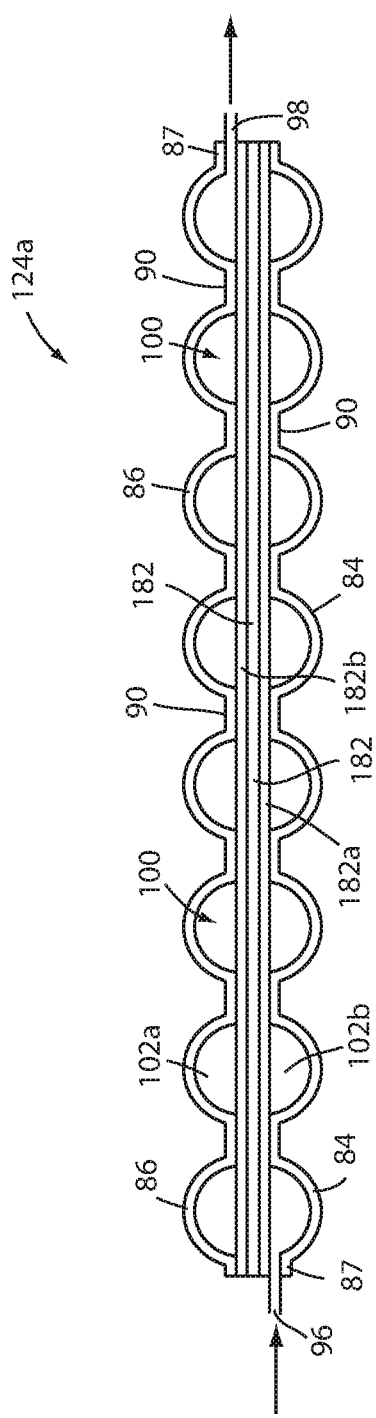
FIG. 7 is a modified version of the thermal pad embodiment of FIGS. 5-6.

FIG. 7 illustrates a modified embodiment of a thermal pad 124a that may be used with thermal control system 20 in place of one or more of thermal pads 24 and/or 124. Thermal pad 124a includes a number of components that are common to thermal pads 24 and/or 124 and such components are provided with the same reference number. Unless otherwise stated explicitly below, the common components are constructed and operate in the same manner previously described, serve the same functions previously described, and may be modified in any one or more of the previously described manners. Thermal pad 124a also includes one or more components that are similar to components of thermal pad 24 and/or 124, but modified in some manner. Such modified components are labeled with the same reference number followed by the letter "a." Those components of thermal pad 124a that are not found in thermal pads 24 or 124 and/or that were not previously described or assigned a reference number are provided with a new reference number.

Thermal pad 124a differs from thermal pad 124 in that its filter 182 has been supplemented with two additional filters 182a and 182b. That is, thermal pad 124a includes, in addition to filter 182, a first outer filter 182a, and a second outer filter 182b. First outer filter 182a is positioned on a first side of filter 182 and second outer filter 182b is positioned on a second side of filter 182 opposite the first side. In this manner, filter 182 is sandwiched between outer filters 182a and 182b such that fluid flowing through filter 182 (in the direction from inlet 96 to outlet 98) must first flow through first outer filter 182a before reaching filter 182. After passing through filter 182, the fluid must then flow through second outer filter 182b before it is able to exit out of outlet 98. In at least one embodiment, first and second outer filters 182a and 182b are laminated on opposite sides of filter 182. In other embodiments, one or more of first and second outer filters 182a and/or 182b may be spaced apart from filter 182.

Regardless of the specific physical arrangement of filters 182, 182a, and 182b, the outer filters 182a and 182b are selected to include a larger pore size than the pore size of filter 182 that is positioned between them. Thus, the outer filters 182a and 182b allow larger particles to pass through them than are able to pass through the intermediate filter 182. Outer filters 182a and/or 182b therefore act as pre-filters and filter out larger suspended particulates from the fluid before the fluid is able to pass through filter 182. This reduces the amount of particulate build-up that might otherwise occur on filter 182, thereby extending the useful life of filter 182. In some embodiments, filter 182 is a 0.2 micron filter adapted to substantially filter out particles having a size larger than 0.2 microns, and outer filters 182a and/or 182b are filters with a larger pore size than 0.2 microns. In many embodiments, outer filters 182a and 182b have the same pore size rating.

By including two outer filters 182a and 182b, thermal pad 124a ensures that the fluid flowing therethrough is always pre-filtered by either outer filter 182a or 182b, regardless of which direction the fluid flows through pad 124a. That is, thermal pad 124a is configured to be agnostic as to the direction of fluid flow so that a user can couple either inlet 96 to outlet port 44 of thermal control unit 22, or outlet 98 to outlet port 44 of thermal control unit 22. By being direction agnostic, the user does not have to concern himself or herself with which end (outlet/inlet) of thermal pad 124a he or she couples to outlet ports 44 of thermal control unit 22 because one of the outer filters 182a or 182b will always pre-filter the fluid before it reaches filter 182. This makes the coupling of thermal pad 124a to thermal control unit 22 easier. However, if thermal pad 124a were to be modified such that a specific one of its connectors 78 needed to be coupled to outlet port 44 and the other connector 78 needed to be coupled to inlet port 52, thereby ensuring that fluid always flowed through pads 124a in a known and constant direction, pad 124a could be modified, if desired, to include only one of the outer filters 182a or 182b (whichever one is upstream of filter 182). In such embodiments, the outer filter 182a or 182b that was downstream of filter 182 (which has a smaller pore size) could be omitted because such a downstream filter would not serve an evident purpose.

FIGS. 8-10 illustrate an alternative embodiment of a thermal pad 224 that may be used with thermal control system 20 in place of one or more of thermal pads 24 and/or 124. Thermal pad 224 includes a number of components that are common to thermal pads 24 and/or 124 and such components are provided with the same reference number. Unless otherwise stated explicitly below, the common components are constructed and operate in the same manner previously described, serve the same functions previously described, and may be modified in any one or more of the previously described manners. Thermal pad 224 also includes one or more components that are similar to components of thermal pad 24 and/or 124, but modified in some manner. Such modified components are labeled with the same reference number increased into the two hundred range. Those components of thermal pad 224 that are not found in thermal pads 24 or 124 and/or that were not previously described or assigned a reference number are provided with a new reference number.

Thermal pad 224 differs from thermal pad 124 primarily in the size of its filter 282 (FIGS. 8-10). More specifically, instead of a filter sheet extending over substantially the entire area of main body portion 80, such as filter 182 does in thermal pad 124, filter sheet 282 extends over approximately only a quarter of the surface area of main body portion 80. Filter sheet 282 otherwise functions in the same manner as filter sheet 182. That is, fluid entering inlet 96 enters a lower half 102b of fluid chamber 100. In order for the fluid to exit out of outlet 98 of main body portion 80, the fluid must travel to the upper half 102a of fluid chamber 100, which means the fluid must pass through filter 282. Accordingly, filter 282 filters the fluid as it circulates through main body portion 200.

Filter 282 is bonded to both first and second sheets 84 and 86 along its top edge 108a, its bottom edge 108b, and its first side 108c (FIG. 8). Filter 282 is also bonded to both first and second sheets 84 and 86 at bonding locations 90. Still further, filter 282 is bonded to first and second sheets 84 and 86 along a portion of its second side 108d that coincides with the upstream-most wall 104 within main body portion 80. In a region 110 of second side 108d between wall 104 and top edge 108a, filter 282 is bonded to only first sheet 84, but not to second sheet 86, as shown more clearly in FIG. 10. By bonding filter sheet 282 to first sheet 84 in this region 110, any fluid that is in lower half 102b of fluid chamber 100 must pass through filter 282 before traveling downstream of region 110, thereby ensuring that all fluid traveling downstream of region 110 is filtered.

It will be understood that the arrangement of outlet 98 and the bonding of filter sheet 282 within region 110 can be reversed from what is shown in FIGS. 8-10. That is, instead of having inlet 96 in direct fluid communication with lower half 102b of fluid chamber 100, inlet 96 could be modified to enter into upper half 102a of fluid chamber 100. Such a modification would be accompanied by changing the bonding of filter 282 in region 110. Specifically, when inlet 96 is modified to enter into upper half 102a, filter 282 is bonded to second sheet 86, rather than first sheet 84, in region 110. This alteration ensures that fluid cannot bypass filter 282 as it flows through passageways 106 toward outlet 98.

It will be understood that the particular size, shape, and location of filter 282 shown in FIGS. 8-10 can be varied significantly. For example, filter 282 may be placed toward the downstream end of main body 80, or it may be placed in a middle region of main body 80. Alternatively, or additionally, filter 282 may have a non-square shape and may be implemented in some embodiments as either larger or smaller. Still further, as with all of the filters disclosed herein that are positioned inside of main body 80, it can be combined with one or more filters positioned in hoses 26 (in segment(s) 72 and/or 74) and/or additional filters positioned within main body 80 (e.g. one or more outer filters, such as filters 182a and/or 182b, may added in a manner similar to that described above with respect to thermal pad 124a). As described above, in any of the embodiments having three or more filters, it may be beneficial to arrange the filter with the smallest pore size between the other two (or more) filters (which may have a common filter pore size) so that the other two filters remove the bulk of the larger particles, thereby extending the life of the smaller-pored filter. Further, as noted previously, by constructing the two other filters so as to have a common pore size, the thermal pad can be coupled to thermal control unit 22 in a direction-agnostic manner (e.g. supply hose 26a can be coupled to inlet 96 or to outlet 98 with return hose 26b coupled to the other of the inlet 96 or outlet 98).

FIGS. 11-13 illustrate an alternative embodiment of a thermal pad 324 that may be used with thermal control system 20 in place of one or more of thermal pads 24, 124, and/or 224. Thermal pad 324 includes a number of components that are common to thermal pads 24, 124, and/or 224 and such components are provided with the same reference number. Unless otherwise stated explicitly below, the common components are constructed and operate in the same manner previously described, serve the same functions previously described, and may be modified in any one or more of the previously described manners. Thermal pad 324 also includes one or more components that are similar to components of thermal pad 24, 124, and/or 224, but modified in some manner. Such modified components are labeled with the same reference number increased into the three hundred range. Those components of thermal pad 324 that are not found in thermal pads 24, 124, or 224 and/or that were not previously described or assigned a reference number are provided with a new reference number.

Thermal pad 324 differs from the previously described thermal pads primarily in the shape of its filter 382 (FIGS. 11-13). More specifically, instead of a substantially planar sheet, such as filters 82, 182, and 282, filter 382 is a bag shaped filter having an interior 111a and an exterior 111b. Interior 111a is defined between a top filter sheet 112a and a bottom filter sheet 112b. Top and bottom filter sheets 112a and 112b are secured to each other about their entire periphery except for a small region where inlet 96 is defined. As can be seen in FIG. 12, top and bottom filter sheets 112a and 112b may also be secured to each other at bonding locations 90 where first and second sheets 84 and 86 are bonded to each other. At locations 90, top and bottom filter sheets 112a and 112b are secured together by the bonding of first and second sheets 84 and 86.

In the particular embodiment illustrated in the drawings, filter 382 is positioned such that fluid entering into main body 80 from inlet 96 enters into the interior 111a of filter 382. In order for the fluid to escape out of the interior 111a into the exterior 111b, the fluid must pass through filter 382. The passage of fluid through either top or bottom filter sheet 112a or 112b filters out particulates having a larger size than the pore sizes of the filter sheets 112a or 112b, which, in at least some embodiments, is 0.2 microns or smaller.

Interior 111a defines a fluid channel 114 that extends into main body 80 for approximately one quarter of the length of main body 80. It will be understood that filter 382 may be modified to extend farther or shorter distances into main body 80 than what is shown in FIG. 11. Expanding the extent of filter 382 provides a greater surface area for the fluid to flow through, while reducing the extent of filter 382 into main body 80 reduces the surface area for the fluid to flow through. In some embodiments, top fluid sheet 112a may be bonded to bottom fluid sheet 112b at one or more additional locations (beyond their peripheries and bonding locations 90). Such additional bonding may include continuous bonds that define one or more walls within bag shaped filter 382. Such filter walls may be selected to better control the flow of fluid through filter 382 and/or main body 80. Thermal pad 324 may further be modified to include multiple bag shaped filters 382, either in addition to, or in lieu of, any of the aforementioned modifications.

In still other modified embodiments of thermal pad 324, one or more foam or other resilient, but fluid permeable, materials may be positioned inside the interior region 111a of one or more of the one or more bag-shaped filters 382. Such materials may be positioned therein in order to prevent the bag-shaped filter from collapsing on itself if the thermal pad 324 is coupled to thermal control unit 22 in such a way that fluid flows in the opposite direction to what is shown in FIG. 12. That is, if fluid flows from the exterior region 111b into the interior region 111a (which is opposite to what is shown in FIG. 12), the fluid pressure may tend to collapse bag-shaped filter 382. By including a resilient, but fluid permeable material within interior region 111a, such collapse is reduced or eliminated. Such resilient material, in some embodiments, enables thermal pad 324 to be coupled to thermal control unit 22 in a manner that is agnostic as to the direction of the fluid flow. In other embodiments, thermal pad 324 may include two bag-shaped filters 382—one coupled to the inlet 96 and one coupled to the outlet 98, and either one of both of the filters 382 may include or omit such resilient material.

FIGS. 14-16 illustrate an alternative embodiment of a thermal pad 424 that may be used with thermal control system 20 in place of one or more of thermal pads 24, 124, 224, and/or 324. Thermal pad 424 includes a number of components that are common to thermal pads 24, 124, 224, and/or 324 and such components are provided with the same reference number. Unless otherwise stated explicitly below, the common components are constructed and operate in the same manner previously described, serve the same functions previously described, and may be modified in any one or more of the previously described manners. Thermal pad 424 also includes one or more components that are similar to components of thermal pad 24, 124, 224, and/or 324, but modified in some manner. Such modified components are labeled with the same reference number increased into the four hundred range. Those components of thermal pad 424 that are not found in thermal pads 24, 124, 224, or 324 and/or that were not previously described or assigned a reference number are provided with a new reference number.

Thermal pad 424 differs from thermal pad 224 (FIG. 8) in that it includes two additional filters. Specifically, thermal pad 424 includes a filter 482, as well as a first outer 482a and a second outer filter 482b (FIGS. 14-16). Filters 482, 482a, and 482b are similar to filters 182, 182a, and 182b of thermal pad 124 (FIG. 6) except that filters 482, 482a, and 482b are spaced apart from each other and positioned in different locations of body 80 of thermal pad 424. Despite these different locations, filters 482, 482a, and 482b act in a similar manner to filters 182, 182a, and 182b. That is, outer filters 482a and 482b act as pre-filters to filter 482 and filter larger particles out of the fluid before they reach filter 482, thereby reducing the number of particles that would otherwise accumulate in filter 482 and thus extending the life of filter 482. As with outer filters 182a and 182b, outer filters 482a and 482b are selected to have a larger pore size than filter 482. In some embodiments, filter 482 has a pore size adapted to substantially filter out particles having a diameter greater than 0.2 microns, while filters 482a and 482b are constructed with a greater pore size.

As can be seen more clearly in FIGS. 15 and 16, when fluid enters inlet 96 of thermal pad 424, it enters into lower half 102b of fluid chamber 100. In order for the fluid to move into a first zone 120 (FIG. 14) of body 80, the fluid must pass through first outer filter 482a. Once the fluid has entered first zone 120, it must pass through filter 482 before entering a second zone 122. Finally, in order for the fluid in second zone 122 to exit out of outlet 98, it must pass through second outer filter 482b. Thermal pad 424 is therefore constructed to ensure that fluid flowing through body 80 must pass through all three filters 482, 482a, and 482b before exiting.

Filters 482, 482a, and 482b are bonded to both first and second sheets 84 and 86 along their top edges 108a, their bottom edges 108b, and their sides 108c (FIG. 14). Filters 482, 482a, and 482b are also bonded to both first and second sheets 84 and 86 at bonding locations 90, as well as along their edges 108d that are coincident with internal walls 104. Still further, each of filters 482, 482a, and 482b is also secured to first sheet 84 and/or second sheet 86 at a plurality of bonding regions 110. Such bonding regions 110 are positioned along the inner peripheries of first and second zones 120 and 122 and ensure that fluid is not able to flow around the respective filters. Filter 482 is also bonded to a center wall 104a (FIGS. 14 & 16).

It will be understood by those skilled in the art that the size and shape of filters 482, 482a, and 482b, as well as the size and shape of bonding regions 110 may vary from what is shown in FIGS. 14-16. Further, as with thermal pad 124a, thermal pad 424 may be modified to include only a single outer filter 482a or 482b if it is constructed such the flow direction of the fluid through the thermal pad 424 is always known and constant (in such embodiments, the filter 482a or 482b that is upstream of filter 482 is retained and the downstream filter is omitted).

Figure 17:
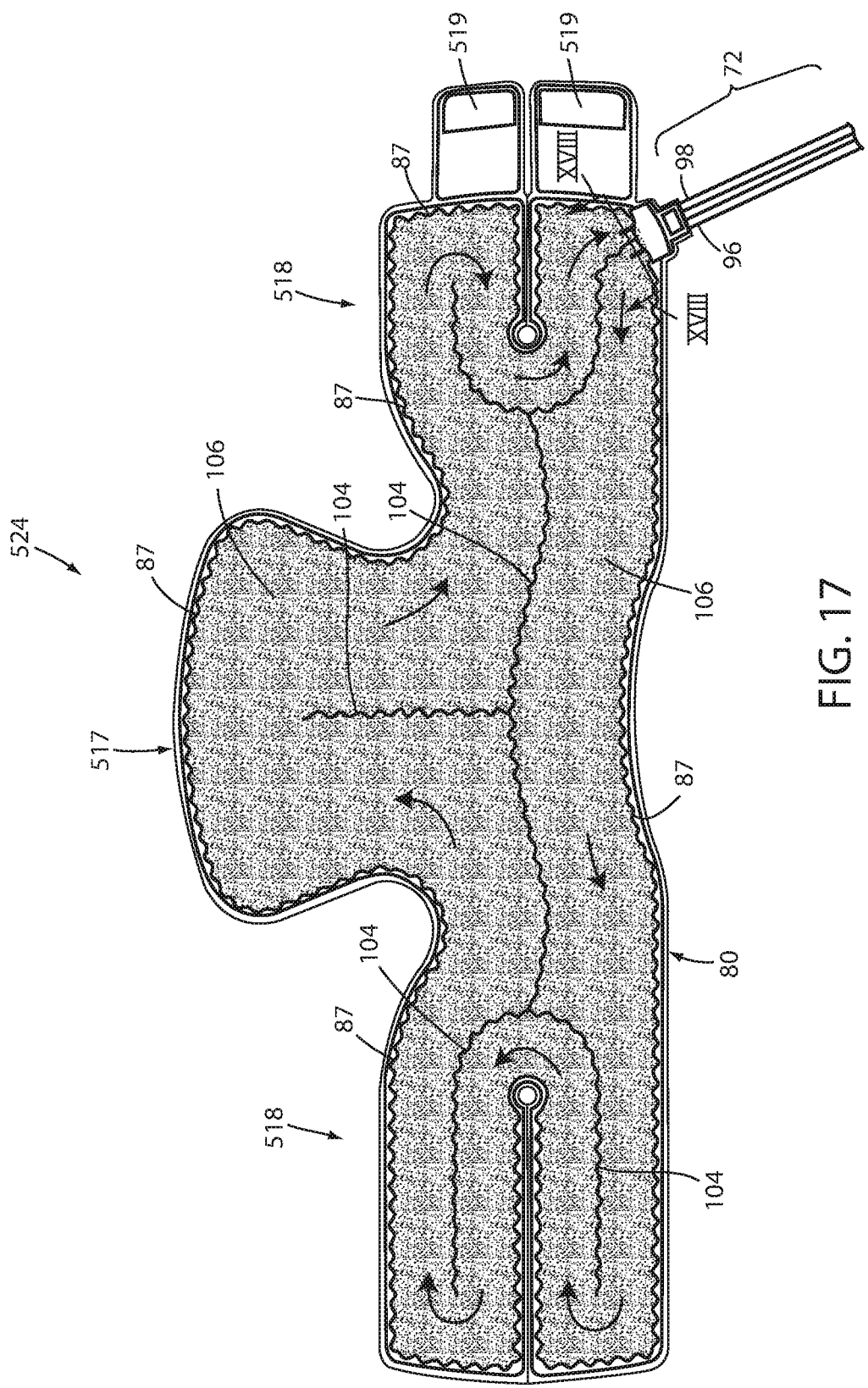
FIG. 17 is a plan view of a fifth alternative embodiment of a thermal pad usable with the thermal control system of FIG. 1.

FIGS. 17-19 illustrate another alternative embodiment of a thermal pad 524 that may be used with thermal control system 20 in place of one or more of thermal pads 24, 124, 224, 324, and/or 424. Thermal pad 524 includes a number of components that are common to thermal pads 24, 124, 224, 324, and/or 424 and such components are provided with the same reference number. Unless otherwise stated explicitly below, the common components are constructed and operate in the same manner previously described, serve the same functions previously described, and may be modified in any one or more of the previously described manners. Thermal pad 524 also includes one or more components that are similar to components of thermal pad 24, 124, 224, 324, and/or 424, but modified in some manner. Such modified components are labeled with the same reference number increased into the five hundred range. Those components of thermal pad 524 that are not found in thermal pads 24, 124, 224, 324, or 424 and/or that were not previously described or assigned a reference number are provided with a new reference number.

Thermal pad 524 differs from the previously described thermal pads in its shape and the locations of its inlet 96 and outlet 98 relative to its body 80, as well as in other respects. Thermal pad 524 includes a central region 517, a pair of wings 518, and one or more fasteners 519 (e.g. hook and loop fasteners, straps, etc.). Central region 517 is intended to be positioned underneath the torso region of a patient (e.g. in contact with the patient's back). Wings 518 are intended to be wrapped around and over the abdominal region of the patient and secured together via the one or more fasteners 519. Central region 517 may also be dimensioned to come into physical contact with all or a portion of the back of a patient's neck. It will be understood that the shape and/or size of thermal pad 524 may be varied from what is shown in FIG. 17. It will also be understood that thermal pad 524 may be used in other regions of a patient's body besides the torso region, such as, but not limited to, the patient's legs, arms, neck, and/or head.

Thermal pad 524 includes an inlet 96 and an outlet 98 that are positioned adjacent to each other. Inlet 96 allows fluid to flow into a fluid passageway 106 that extends throughout thermal pad 524 between inlet 96 and outlet 98. A filter 582 (FIGS. 18 and 19) is included within body 80 of thermal pad 524 and extends over the entire area of body 80. That is, filter 582 is a sheet-like filter that generally defines a plane parallel to a plane generally defined by sheets 84 and 86. The peripheral boundaries of filter 582 generally match, and are sealed to, the peripheral boundaries of body 80. More specifically, filter 582 is bonded at a peripheral seal 87 to first and second sheets 84 and 86. Filter 582 is also bonded to sheets 84 and 86 at internal walls 104 and at bonding locations 90.

As can be seen more clearly in FIGS. 18 and 19, filter 582 is positioned with respect to inlet 96 and outlet 98 such that fluid entering into body 80 from inlet 96 enters on a first side of filter 582 and fluid exiting out of body 80 via outlet 98 is on the second and opposite side of filter 582. Thus, fluid entering into body 80 of thermal pad 524 via inlet 96 must pass through filter 582 before exiting out of outlet 98. FIG. 19 illustrates first sheet 84 and second sheet 86 separated from each other with filter sheet 582 positioned therebetween. As shown therein, it can be seen that filter 582 is positioned over inlet 96 and underneath outlet 98.

FIG. 20 illustrates yet another alternative embodiment of a thermal pad 624 that may be used with thermal control system 20 in place of one or more of the previously discussed thermal pads (e.g. 24-524). Thermal pad 624 includes a number of components that are common to these previously discussed thermal pads and those components are provided with the same reference number. Unless otherwise stated explicitly below, the common components are constructed and operate in the same manner previously described, serve the same functions previously described, and may be modified in any one or more of the previously described manners. Thermal pad 624 also includes one or more components that are similar to one or more components of the previously discussed thermal pads 24, and such modified components are labeled with the same reference number increased into the six hundred range. Those components of thermal pad 624 that are not found in the previously discussed thermal pads are provided with a new reference number.

Thermal pad 624 differs from the previously described thermal pads in that it includes a filter 682 that is alternately bonded to first sheet 84 and second sheet 86. This bonding occurs at locations 690. As can be seen in FIG. 20, this bonding alternates between first sheet 84 and second sheet 86. That is, filter sheet 682 is bonded to only one of first sheet 84 or second sheet 86 at a given bonding location 690, and at the bonding locations 690 adjacent thereto, filter sheet 682 is bonded to the other of the first or second sheets 84 or 86. This alternate bonding occurs not only in the lateral directions illustrated in FIG. 20, but also in the forward and backward directions. In other words, the bond 690 between filter 682 and second sheet 86 shown generally in the middle of FIG. 20 is surrounded not only on its right and left side by bonds 690 to first sheet 84, but also by bonds behind and in front of it (not shown in FIG. 20, but extending into and out of the plane of FIG. 20) that are between filter 682 and first sheet 84. Thus, in this particular embodiment, a given bond 690 to second sheet 86, for example, is surrounded by four adjacent bonds 690 to first sheet 84 (one on each side, one in front and one behind). Similarly, a given bond 690 to first sheet 84 is surrounded by four adjacent bonds 690 to second sheet 86. Other arrangements of bonds 690 may be utilized, including one or more bonds 690 that bond filter 682 to both first and second sheet 84 and 86 at a common location 690. Regardless of the particular bonding layout selected for a given embodiment, fluid entering thermal pad 624 enters into either upper interior region 102a or lower interior region 102b and must pass through filter sheet 682 at some point in order to exit out of thermal pad 624.

Filter sheet 682 is adapted to perform both a structural function and a filtering function in thermal pad 624 (FIG. 20). Filter sheet 682 performs the structural function of keeping first and second sheets 84 and 86 within a set distance of each other. That is, the pressure of the fluid supplied to thermal pad 624 from thermal control unit 22 tends to urge first and second sheets 84 and 86 apart from each other (first sheet 84 is urged upward in the sectional view of FIG. 20 and second sheet 86 is urged downward in FIG. 20). This upward and downward movement is resisted by filter sheet 682 which limits the distance the two sheets 84 and 86 can move apart from each other. Filter sheet 682 therefore serves the structural function of keeping thermal pad 624 from bulging beyond a desired limit, as well as filtering the fluid passing through main body portion 80.

In the example shown in FIG. 20, thermal pad 624 includes an insulating sheet 88 as well as an interior sheet 116. Interior sheet 116 may be made of a non-woven fabric material that is adapted to come into contact with a patient's skin. In some embodiments, the non-woven fabric material of interior sheet 116 is impregnated with one or more materials having anti-microbial properties. Such materials include, but are not limited to, copper, silver, zinc, and other anti-microbial metals, both in pure form (including, but not limited to, nanoparticle and/or nanotube form) and mixed with other components (e.g. silver salts, silver-polymer composites, silver-impregnated zeolites, etc.). Other materials also include polyethylene glycol, chitosan, quaternary ammonium compounds, polyethyleneimine, polyguanidines, organosilanes, biguanide-based polymers, and/or halogen-containing polymers. Still other materials may embedded within insulating sheet 88 in order to reduce and/or eliminate the presence of microbes, as would be known to one of ordinary skill in the art.

It will be understood that thermal pad 624 may also be modified to include antimicrobial materials embedded in first sheet 84. The addition of antimicrobial materials within first sheet 84 helps to reduce or eliminate the possibility of microbes living between interior sheet 116 and first sheet 84.

This is particularly helpful when interior sheet 116 is made of a non-woven material that is liquid and/or air permeable and it is possible for particles to enter into the space between interior sheet 116 and first sheet 84. By including antimicrobial materials in first sheet 84 and/or interior sheet 116, the risk of transferring an infectious agent from or to a patient via thermal pad 624 is reduced.

It should also be noted that, by including antimicrobial materials within first sheet 84, fluid flowing within fluid chamber 100 will come into contact with the interior of first sheet 84 and the antimicrobial properties embedded therein. Such contact may help to kill microbes within the fluid circulating through thermal pad 624. To that end, second sheet 86, in some embodiments, is also embedded with antimicrobial particles. The presence of antimicrobial materials in sheets 84 and 86 therefore helps to kill microbes not only on the surfaces external to these sheets, but also the internal surfaces that come into contact with the circulating fluid.

Thermal pad 624 may further be modified to include antimicrobial materials embedded within filter 682. Such antimicrobial materials help to kill any microbes that get trapped within filter 682. Filter 682 therefore not only filters out microbes (and any other particles exceeding its pore size), but also helps to kill the trapped microbes.

In some embodiments, thermal control unit 22 is modified to include one or more fluid pressure sensors that determine the pressure difference between outlet port 44 and inlet 52. In such embodiments, controller 46 monitors this pressure difference and, if it exceeds a threshold, provides an alert to the user that the filter within the pad (24, 124, 224, etc.) may need to be changed. The threshold is chosen, in at least some embodiments, such that controller 46 is able to distinguish between high pressure differences due to an obstructed filter and high pressure differences due to a completely, or nearly completely obstructed thermal pad (the latter generating an even higher pressure difference than the former). That is, controller 46 is configured, in at least some embodiments, to issue a first alert when a filter should be changed and to issue a second and different alert when the thermal pad is completely, or nearly completely, obstructed. In some embodiments, controller 46 determines that the thermal pad is completely, or nearly completely, obstructed by monitoring for pressure differences between the outlet and inlet ports 44 and 52 that exceed a second threshold that is higher than the threshold used to detect an obstructed filter. In other embodiments, controller 46 determines that the thermal pad is completely or nearly completely obstructed by using one or more flow sensors that measure flow rates of fluid exiting outlet port(s) 44 and/or entering inlet port(s) 52.

It will be understood by those skilled in the art that any of the features, functions, and/or structures of any of the thermal pads discussed herein can be combined with any one or more of the features, functions, and/or structures of any of the other thermal pads discussed herein. Thus, as but one non-limited example, it will be understood that, although thermal pad 624 was the only thermal pad discussed above in which antimicrobial materials may be integrated into its filter, any of the other thermal pads 24, 124, 224, 324, 424, and/or 524 may utilize one or more filters having antimicrobial materials integrated therein. As yet another example, although thermal pad 624 was the only thermal pad discussed above having an interior sheet 116, such a sheet may be added to any of the other thermal pads discussed herein. Still other combinations of features, functions, and structures are possible and contemplated by this disclosure.

It will also be understood by those skilled in the art that the previous discussions of filter pores and filter ratings may refer to several different measurements. For example, filters may commonly have a nominal filter rating, an absolute filter rating, and/or a mean filter rating. In some situations, filters may also or alternatively have a beta ratio rating, which refers to the ratio of the number of particles of a particular size upstream of the filter compared to the number of particles of that particular size downstream of the filter. The foregoing discussion of filter pores and/or filter ratings may include any of these potential measurements and/or ratings so long as the fluid that is filtered by filters 82 (and/or 182, 282, etc.) removes a sufficient amount of particles of 0.2 microns or larger after a suitably short time duration and/or after a suitably small number of circuits through thermal pads 24. What is considered sufficient and suitable may vary from application to application, and/or may be dictated by one or more governing institution, such as, but not limited to, the U.S. Food and Drug Administration (FDA).

Any of thermal pads 24, 124, 224, etc. discussed above may further be modified to include one or more sensor layers positioned adjacent to first sheet 84. Such a sensing layer includes one or more sensors that are adapted to be placed in contact with the skin of a patient whose temperature is to be controlled. The specific type(s) and number of sensors incorporated into the sensor layer may vary from embodiment to embodiment. In some embodiments, the sensor layer includes at least one sensor that is a tissue oxygenation sensor adapted to detect changes in the amount of oxygen in the patient's tissue adjacent the sensor. Although different types of tissue oxygenation sensors may be used, one suitable type is disclosed in commonly assigned U.S. patent application Ser. No. 14/884,222 filed Oct. 15, 2015, by inventors Marko Kostic et al. and entitled SYSTEMS AND METHODS FOR DETECTING PULSE WAVE VELOCITY, the complete disclosure of which is incorporated herein by reference. Another suitable oxygenation sensor is disclosed in commonly assigned U.S. patent application Ser. No. 15/200,818 filed Jul. 1, 2016, by inventors Marko Kostic et al. and entitled SYSTEMS AND METHODS FOR STROKE DETECTION, the complete disclosure of which is also incorporated herein by reference. Still other types of tissue oxygenation sensors may also be used. Further, in some embodiments, multiple tissue oxygenation sensors are included in the sensor layer.

Any of thermal pads 24, 124, 224, 324, 424, and/or 524 may also be modified to be shaped the same as, or similar to, the shape of thermal pad 624. That is, any of the bodies 80 of pads 24, 124, 224, 324, 424, and/or 524 may be modified to include a central region with a pair of wings, such as the central region 517 and wings 518 of thermal pad 524. Fasteners may also be added in order secure the thermal pad in contact with the patient's body.

Still other additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A thermal pad adapted to be placed in physical contact with a patient and to receive temperature controlled fluid for controlling the patient's temperature, the thermal pad comprising:
   a first sheet adapted to face toward the patient;
   a second sheet adapted to face away from the patient;
   a peripheral seal coupling a periphery of the first sheet to a periphery of the second sheet to thereby define a fluid chamber between the first and second sheets;
   a fluid inlet into the fluid chamber;
   a fluid outlet out of the fluid chamber;
   a first connector adapted to releasable couple to a supply hose from a thermal control unit;
   a second connector adapted to releasably couple to a return hose of the thermal control unit;
   an inlet hose segment having a first end coupled to the first connector and a second end coupled to the fluid inlet such that the inlet hose segment cannot be decoupled from the first connector or the fluid inlet without damage;
   an outlet hose segment having a first end coupled to the second connector and a second end coupled to the fluid outlet such that the outlet hose segment cannot be decoupled from the second connector or the fluid outlet without damage; and
   a filter adapted to filter temperature-controlled fluid supplied from the thermal control unit as it passes through the thermal pad, wherein the filter is positioned in at least one of the following locations: (a) inside the inlet hose segment, (b) inside the outlet hose segment, or (c) inside the fluid chamber.

2. The thermal pad of claim 1 further comprising a second filter, wherein the filter is positioned in the inlet hose segment and the second filter is positioned in the outlet hose segment.

3. The thermal pad of claim 2 further comprising a third filter positioned within the fluid chamber.

4. The thermal pad of claim 3 wherein the third filter has a different pore rating than the filter and the second filter.

5. The thermal pad of claim 4 wherein the third filter is a filter sheet coupled to the first and second sheets by a plurality of bonds.

6. The thermal pad of claim 1 wherein the filter is positioned inside the inlet hose segment or inside the outlet hose segment.

7. The thermal pad of claim 1 wherein the filter is positioned inside the fluid chamber.

8. The thermal pad of claim 7 wherein the filter includes a filter sheet having a first surface facing toward the first sheet and a second surface facing toward the second sheet, the filter sheet positioned within the fluid chamber such that fluid entering the fluid inlet must pass through the filter sheet before exiting out of the fluid outlet.

9. The thermal pad of claim 8 wherein the filter sheet, the first sheet, and the second sheet are all substantially parallel to each other; and wherein the filter sheet, the first sheet, and the second sheet all have a surface area of substantially the same magnitude.

10. The thermal pad of claim 8 further comprising a plurality of bonds, each of the bonds coupling the first sheet, second sheet and filter sheet together; and wherein the first sheet and the second sheet each have a surface area of substantially the same magnitude and the filter sheet has a surface area less than the magnitude of the first and second sheets.

11. The thermal pad of claim 10 wherein the filter is a bag shaped filter having an interior that defines a fluid channel that extends into the thermal pad; and wherein the bag shaped filter includes a top filter sheet and a bottom filter sheet and the plurality of bonds also bond the top filter sheet and the bottom filter sheet to each other and to the first sheet and the second sheet.

12. The thermal pad of claim 8 wherein the filter sheet is adapted to filter particles having a size of 0.2 microns or larger; and wherein the thermal pad further comprises a second filter sheet adapted to filter particles larger than 0.2 microns and to allow particles of 0.2 microns to pass there through.

13. The thermal pad of claim 8 wherein the first surface of the filter sheet is secured to the first sheet at a first plurality of locations and the second surface of the filter sheet is secured to the second sheet at a second plurality of locations different from the first plurality of locations; and wherein the thermal pad further comprises a non-woven sheet positioned adjacent the first sheet and adapted to come into contact with the patient, wherein both the non-woven sheet and the first sheet are embedded with antimicrobial substances.

14. The thermal pad of claim 7 wherein the filter includes antimicrobial substances embedded therein, the antimicrobial substances adapted to come into contact with and kill microbes filtered by the filter.

15. The thermal pad of claim 7 wherein the filter defines a fluid channel that extends into the thermal pad, and wherein the filter is made of a material that stretches in response to a first threshold pressure of the fluid, the first threshold pressure being less than a second threshold pressure required to cause the first and second sheets to stretch.

16. The thermal pad of claim 7 further comprising a second filter positioned inside the fluid chamber, wherein both the filter and the second filter define first and second channels that extend a distance into the thermal pad.

17. The thermal pad of claim 16 wherein both the filter and the second filter are each bag shaped.

18. The thermal pad of claim 1 wherein the first sheet is constructed of a material having antimicrobial substances embedded therein, and wherein the thermal pad further comprises a non-woven sheet positioned adjacent the first sheet and adapted to come into contact with the patient, wherein the non-woven sheet is also embedded with antimicrobial substances.

19. The thermal pad of claim 1 further comprising:
   a second filter positioned in fluid communication with the fluid chamber; and
   a third filter positioned in fluid communication with the fluid chamber and between the filter and the second filter such that fluid flowing through the filter must pass through the third filter before reaching the second filter;
   wherein the filter and the second filter both have a common pore rating for filtering particles of a first size, and the third filter has a pore rating for filtering particles of a second size, the second size being smaller than the first size.

20. The thermal pad of claim 19 wherein the third filter has a pore rating for filtering particles having a size of 0.2 microns or larger and the filter and the second filter both have a pore rating for allowing particles having a size of greater than 0.2 microns to pass therethrough.

* * * * *